(12) United States Patent
Dam

(10) Patent No.: US 11,000,623 B2
(45) Date of Patent: May 11, 2021

(54) PERSONAL AIR TREATMENT SYSTEM AND METHOD

(71) Applicant: Tuan Quoc Dam, Round Rock, TX (US)

(72) Inventor: Tuan Quoc Dam, Round Rock, TX (US)

(*) Notice: Subject to any disclaimer, the term of this patent is extended or adjusted under 35 U.S.C. 154(b) by 476 days.

(21) Appl. No.: 15/791,164

(22) Filed: Oct. 23, 2017

(65) Prior Publication Data

US 2019/0117820 A1    Apr. 25, 2019

(51) Int. Cl.
| | |
|---|---|
| *A61L 9/00* | (2006.01) |
| *A61L 9/20* | (2006.01) |
| *A61L 9/012* | (2006.01) |
| *A62B 23/02* | (2006.01) |
| *B03C 3/32* | (2006.01) |
| *B03C 3/82* | (2006.01) |
| *B03C 3/38* | (2006.01) |
| *F24F 11/30* | (2018.01) |
| *F24F 11/62* | (2018.01) |
| *F24F 3/16* | (2021.01) |
| *F24F 11/56* | (2018.01) |
| *F24F 120/10* | (2018.01) |
| *F24F 110/50* | (2018.01) |
| *A62B 18/00* | (2006.01) |
| *F24F 8/22* | (2021.01) |
| *F24F 8/50* | (2021.01) |

(52) U.S. Cl.
CPC ............... *A61L 9/20* (2013.01); *A61L 9/012* (2013.01); *A62B 23/025* (2013.01); *B03C 3/32* (2013.01); *B03C 3/383* (2013.01); *B03C 3/82* (2013.01); *F24F 3/16* (2013.01); *F24F 11/30* (2018.01); *F24F 11/62* (2018.01); *A62B 18/006* (2013.01); *F24F 8/22* (2021.01); *F24F 8/50* (2021.01); *F24F 11/56* (2018.01); *F24F 2110/50* (2018.01); *F24F 2120/10* (2018.01); *F24F 2221/38* (2013.01)

(58) Field of Classification Search
CPC ......... A61L 9/20; A61L 9/012; A62B 23/025; B32B 27/08; A41D 31/0016; A41D 13/1138
USPC ......... 2/410; 422/306; 55/DIG. 35, DIG. 33; 128/200.24
See application file for complete search history.

(56) References Cited

U.S. PATENT DOCUMENTS

| | | | |
|---|---|---|---|
| 2003/0105407 A1* | 6/2003 | Pearce, Jr. | A61B 5/083 600/532 |
| 2008/0192459 A1* | 8/2008 | Kwok | A61B 5/1116 362/105 |
| 2017/0086504 A1* | 3/2017 | Cameron | A24F 47/008 |

* cited by examiner

*Primary Examiner* — Monzer R Chorbaji
(74) *Attorney, Agent, or Firm* — Kirk Dorius; Dorius Law PC

(57) ABSTRACT

A personal air treatment device is used to treat air with UV irradiation and with scents. The scents may be used as an attractant or masking for hunting. Multiple devices may be controlled by a smartphone application to strategically alter scent dispersion according to local wind patterns, user location, and relative device location. Similar air treatment devices may be integrated with a particulate mask or used to otherwise treat the air around a user.

17 Claims, 25 Drawing Sheets

PERSONAL AIR TREATMENT SYSTEM AND METHOD

FIELD OF INVENTION

This invention generally relates to air treatment, and in particular, to scenting and/or ultraviolet (UV) treatment of air around a user.

BACKGROUND OF THE INVENTION

UV can effectively neutralize airborne pathogens, however, UV air treatment devices have historically been too bulky and power-hungry for personal portable use.

Scenting devices are commonly used in hunting to mask the scent of the hunter or draw in animals within shooting range. This typically involves fixing one or more passive scent dispensers to a tree and/or carried on the hunter's person. More advanced scenting systems may include a battery and impeller to better disperse scents. These passive and active devices lack remote user controls or other advanced features to accommodate changes in wind conditions and the like. Accordingly, improvements are sought in scenting devices and personal air purification devices.

SUMMARY OF THE INVENTION

While the way that the present invention addresses the disadvantages of the prior art will be discussed in greater detail below, in general, the present invention provides a small portable wearable device that uses UV-C to inactivate or neutralize airborne pathogens such as viruses that cause cold and influenza, mold spores, MRSA, C-diff, VRE, Zika virus, MERS, SARS, and the like.

One aspect of the invention features, in some embodiments, an apparatus for UV treatment of air. The apparatus includes an enclosure housing an air impeller, power supply, UV source, and control circuit. The enclosure defines an air inlet and an air outlet and a circuitous path or irradiation chamber therebetween, to afford sufficient dwell time of the air under UV exposure to inactivate any pathogens entrained in the air.

In some embodiments, a reflective material disposed along the air pathway serves to redirect and disperse UV radiation. In some cases, the reflective material forms one or more boundaries of the air pathway. In some cases the reflective material is coated onto the floor, ceiling, or sidewalls of the air pathway. In some cases, a surface coating inhibits the growth of pathogens within the device.

One aspect of the invention features, in some embodiments, a scent cartridge/dispenser along the pathway. In some embodiments, the scent dispenser includes a removable slide to allow for insertion of slide inserts or cartridges of various scents, fragrances, aroma-therapy effects, or the like. In some embodiments, a scent slide allows the user to insert a variety of fragrance cartridges including but not limited to citronella (to prevent mosquito bites), lavender (to reduce stress), aloe, musk (to attract animals or mask scents for hunting). In some embodiments, the scent slide can be positioned adjacent a heat source in the enclosure to increase scent release. In some cases, the scent cartridge is configured as film, pellet, gauze or absorbent material configured to release an oil-based or water-based scent. In some cases, the scent cartridge is heated to increase scent release.

One aspect of the invention features, in some embodiments, a light emitting diode (LED) source of UV-C radiation. A glass diffuser helps to scatter the UV throughout the pathway, irradiation chamber, or device enclosure. The low-power consumption of the LED-UV affords increase battery life and operational time.

In some embodiments, the UV device is sized and configured to be worn so as to direct air towards the user's face. For example, the UV device can be worn about the neck on a lanyard, clipped to the neckline of a shirt, or attached to or integrated into a hat. In some embodiments this personal UV device can travel anywhere and can be attached to custom designed accessories such as a lanyard, desk mount, car visor, belt loop, clip to facilitate use during travel, exercise, while working, or for use on a baby stroller or car seat. Similarly, the UV device may include a stand so as to be directed upwards towards the user from a nearby work surface.

In some embodiments, the scent dispersal device may be part of a system of remote controllable devices. In some cases, multiple scent dispersal devices may be positioned remote from a user and may be controllable by the user, e.g., via Bluetooth. In some embodiments, a smartphone application monitors local wind condition data available over the internet and varies the operation of the various scent devices accordingly. Users may select from any number of preprogrammed settings, e.g., timed, pulsed, random, alternating, escalating, calendared, and the like. Similarly, users may establish any number of custom settings for individual or groups of devices. For example, users may group devices for collective setting adjustments or may establish settings for individual devices. The software application may log usage data to inform broader user community settings or to recommend user-based personalized settings, and the like.

Another aspect of the invention features, in some applications, a method of dispersing scents with a personal scenting device. The method includes passing air through a personal scenting device along an air pathway exposed to a scent reservoir. In some applications, the method includes coordinating multiple scent dispersal devices to achieve a desired regional scenting effect in the region around the user, within a stand of trees to which a hunter wishes to attract an animal. In some applications, the devices are controllable wirelessly using a smartphone application providing user selectable settings for individual devices and groups of devices.

In some implementations, the UV device itself includes a display and/or user interface. In some cases, the display presents an operational status indicator, battery level indicator, connectivity status, duration of operation, and the like. In some implementations, the UV device includes at least one battery charging port and a data port. In some implementations, the UV device includes a near-field charger.

One aspect of the invention features, in some embodiments, a HEPA filter or aroma dispenser positioned at one of the inlet and the outlet, or along the air pathway therebetween. In some embodiments, the HEPA filter can be scented, e.g., by addition of oils or other extracts.

In some embodiments, the personal air purification device is integrated with or attached to a face mask filter such as N95 respirator masks. For example, the personal air purification device may attach to an air inlet formed in the side of an N95 respirator mask.

Another aspect of the invention features, in some applications, a method of purifying air with a personal UV device. The method includes passing air through a personal UV device along a circuitous air pathway under exposure to UV from an LED UV source. The method further includes dispersing the UV along the circuitous air pathway via a reflective material to provide sufficient UV exposure, or dwell time, to substantially inactivate airborne pathogens.

In some embodiments, a timer control cycles the air impeller and UV source to provide a region of treated air about the user's person while conserving energy. In some embodiments, the LED UV and air impeller may be operated at slightly different times, e.g., alternately pulsed.

In some embodiments, the personal UV device is sized and configured to treat at least the volume of air breathed by a user, in some cases, multiples of that volume. For example, an impeller sized to operate at 20 cfm would treat 7-20 times the volume of air used by during respiration by one user. In some embodiments, a motion detector can determine when a user is walking or otherwise moving and can adjust the UV device operation accordingly, e.g., to increase airflow.

One aspect of the invention features, in some embodiments, a portable personal air treatment device. The device includes an enclosure defining an air pathway, an impeller for moving air along the air pathway, a UV source disposed along the air pathway to irradiate pathogens entrained in air within the pathway, and a scent cartridge disposed along the air pathway and configured to disperse a scent into air moving within the pathway.

In some embodiments, integrated within a personal particulate mask and configured to treat air within the particulate mask. In some embodiments, the device further includes a near-field charger.

In some embodiments, the device further includes a processor programmed for logging usage data. In some cases, the usage data comprises one or more of duration of use, time of use, frequency of use, air quality, and geolocation.

In some embodiments, the device further includes a wireless transponder for communicating one or more of a performance parameter, software update, and usage data. In some embodiments, the personal air treatment device is configured to be controllable via the wireless transponder. In some embodiments, the personal air treatment device is configured to control an operational status of a plurality of networked personal air treatment devices.

In some embodiments, the scent cartridge is configured to be highly absorbent of oils and to release the oil by evaporation into the air pathway. In some embodiments, the scent cartridge is exposed to the airflow in the air pathway and is substantially hermetically sealed across scent cartridge surfaces not exposed to the airflow.

Another aspect of the invention features, in some embodiments, a system for scenting air within a region. The system includes a plurality of portable air treatment devices controllable via a wireless protocol to disperse a scent into the air around the air treatment devices and a controller having a processor programmed to control the plurality of portable air treatment devices via the wireless protocol. The processor is programmed to selectively alter a performance parameter of one or more of the plurality of the portable air treatment devices based on at least one of local weather data, wind direction and location relative to a user.

In some embodiments, the processor is programmed to selectively alter at least one of the power state, impeller rate, temperature, and UV irradiation level of a subset of the plurality of portable air treatment devices. In some embodiments, the processor is programmed to receive user input regarding performance parameter settings for one or more of the plurality of portable air treatment devices.

In some embodiments, the processor is programmed to automatically adjust the performance parameter of one or more of the plurality of the portable air treatment devices. In some embodiments, the processor is programmed to coordinate performance parameters of the plurality of portable air treatment devices based on the location of a central user device. In some embodiments, the processor is programmed to coordinate performance parameters of the plurality of portable air treatment devices based on at least one of wind conditions, air quality conditions, and geolocation data. In some embodiments, the processor is programmed to coordinate preprogrammed performance parameters of the plurality of air treatment devices including at least one of timed, pulsed, random, alternating, escalating, and calendared device operation.

Another aspect of the invention features, in some embodiments, a personal air treatment mask including a particulate mask and an air treatment device disposed within the particulate mask. The air treatment device includes an enclosure defining an air inlet, an air outlet, and an air pathway therebetween, an impeller for conducting air along the air pathway; and a UV lamp disposed along the air pathway to treat air circulated within the particulate mask.

In some embodiments, the air treatment device further comprises a replaceable scent cartridge disposed along the air pathway. In some embodiments, the air treatment device further includes a wireless transponder configured to communicate usage data for the air treatment device via a wireless protocol.

In some embodiments, the personal UV device includes wireless connectivity features, e.g., Bluetooth, for remote tracking of usage data. Usage data can be stored for later upload via wired connection or when the device comes in range of a suitable network connection. In some embodiments, multiple personal UV devices in a vicinity may be paired using Bluetooth Low Energy (BLE) to communicate with each other or with a central network to vary or coordinate operational parameters based on the number and proximity of other personal UV devices.

In some embodiments, a mobile device such as a smartphone can be synchronized with the personal UV device and a mobile application can show personal, regional, or global usage data. For example, the application can provide an estimate of the total operational time in a given period, the volume of air treated in that time period, the number of pathogens inactivated in that time period, provide real time data visibility of pollen count based on the geographical location of the user through GPS, and the like. Onboard particulate sensors can also provide estimates of air quality.

Accordingly, a personal air treatment device is disclosed that offers advantages of scent dispersion, UV inactivation of pathogens, reduced air pollution, aromatherapy, and usage tracking with a portable battery-operated device.

BRIEF DESCRIPTION OF THE DRAWINGS

A more complete understanding of the present invention may be derived by referring to the detailed description and claims when considered in connection with the Figures, wherein like reference numerals refer to similar elements throughout the Figures, and FIG. 1 illustrates a perspective view of a personal air treatment device according to one embodiment;

FIG. 2 illustrates a front view of the personal air treatment device of FIG. 1;

FIG. 3 illustrates a side view of the personal air treatment device of FIG. 1;

FIG. 4 illustrates a side view of the personal air treatment device of FIG. 1;

Figure 24:
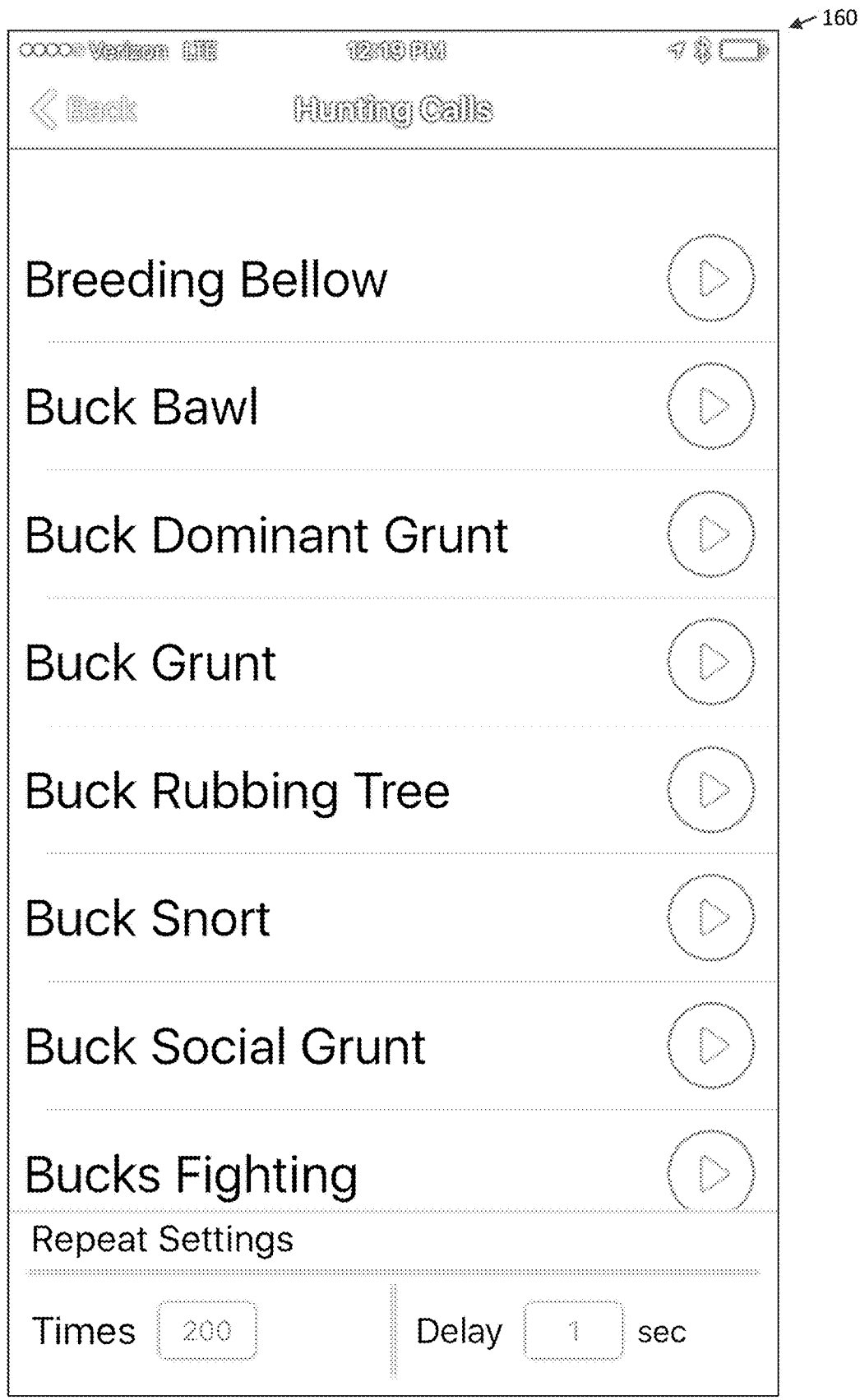
FIG. 24 illustrates a screenshot of an Animal Call feature of the application.
Figure 25:
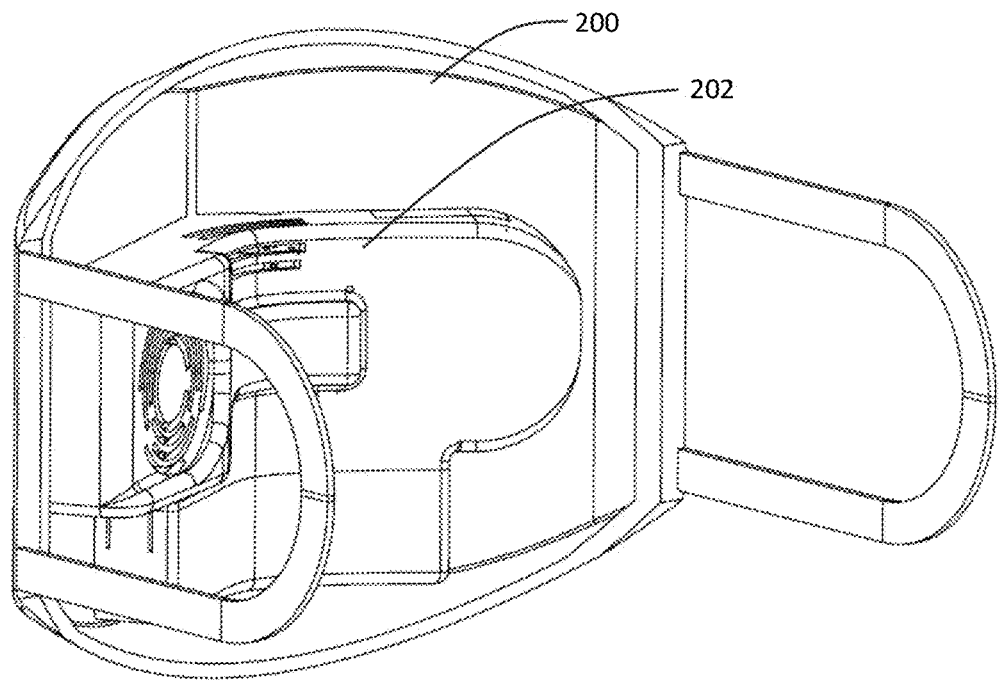
FIG. 25 illustrates a personal air treatment device integrated with a personal particulate mask.
Figure 26:
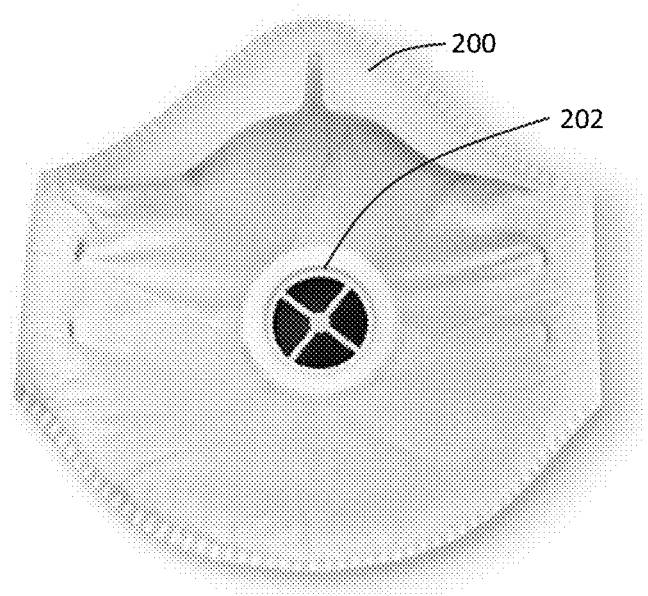
FIG. 26 illustrates a front view of the personal particulate mask of FIG. 25.
Figure 29:
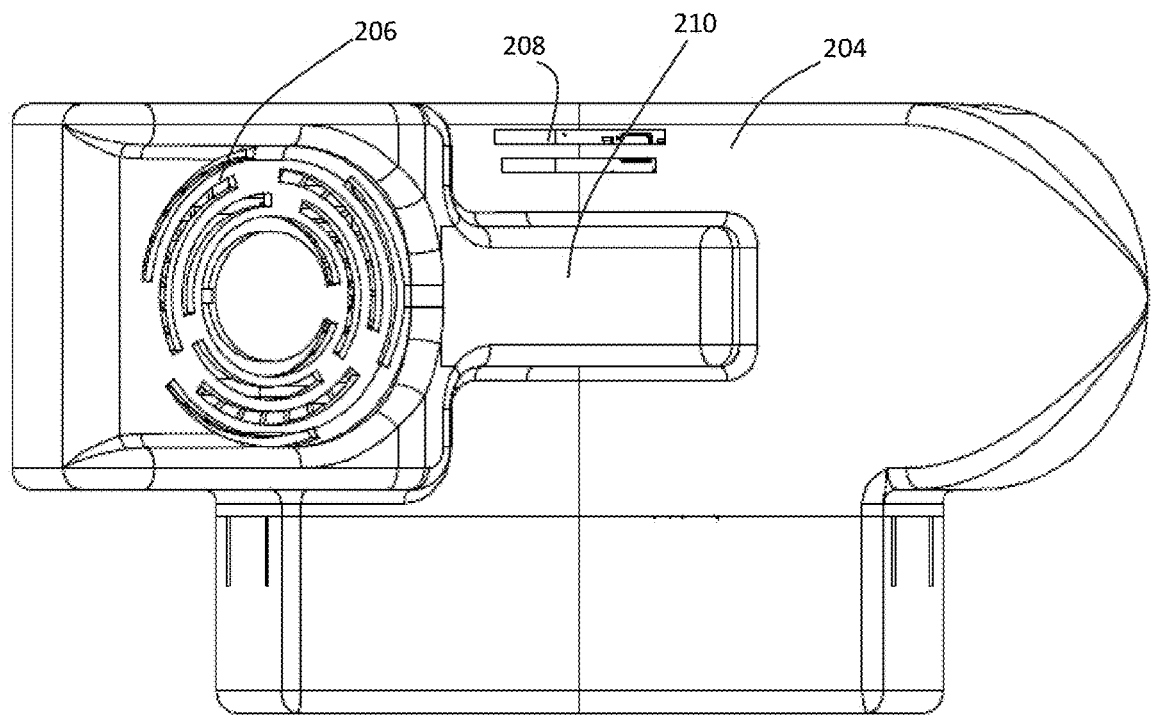

FIG. 29. shows a front view of an enclosure for a personal UV device for use with the particulate mask of FIGS. 24-26.

Figure 30:
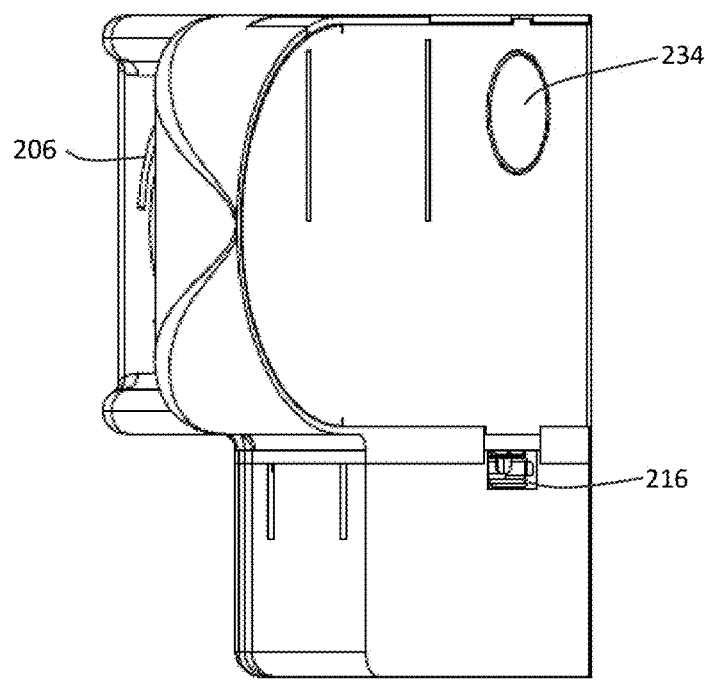

FIG. 30. shows a top view of an enclosure for a personal UV device for use with the particulate mask of FIGS. 24-26.

Figure 31:
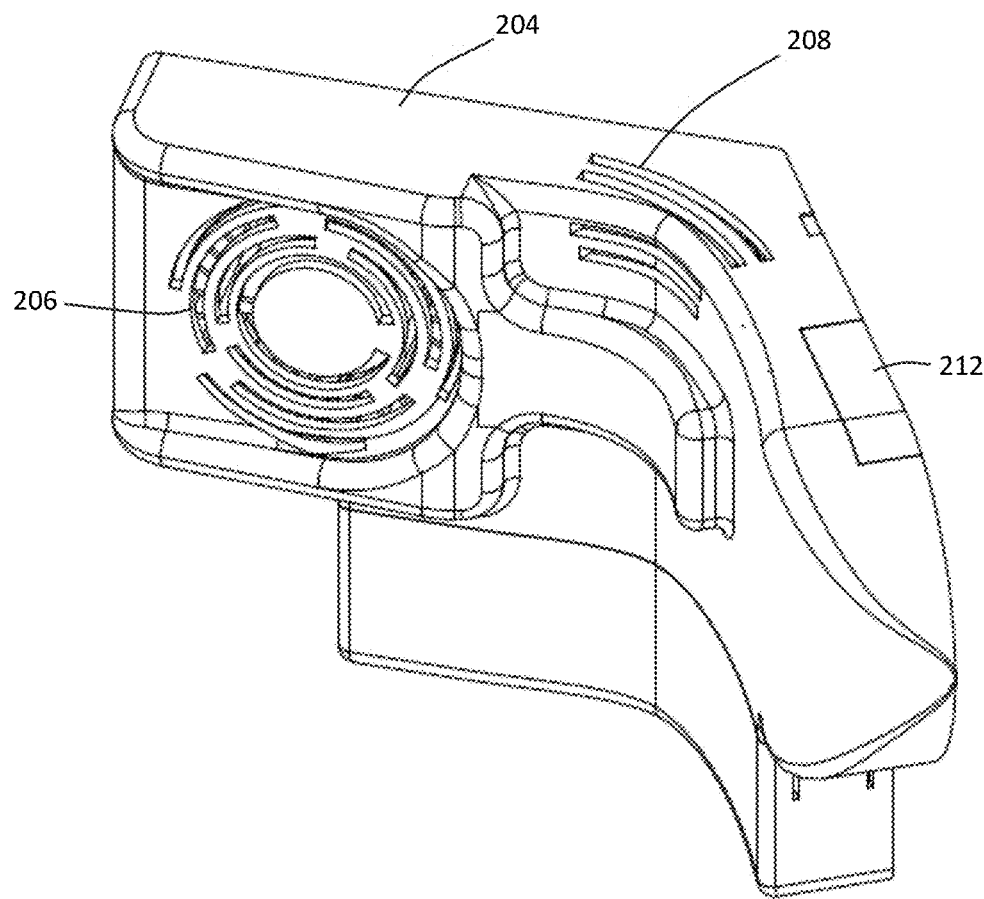

FIG. 31. shows a front perspective view of enclosure for a personal UV device for use with the particulate mask of FIGS. 24-26.

Figure 32:
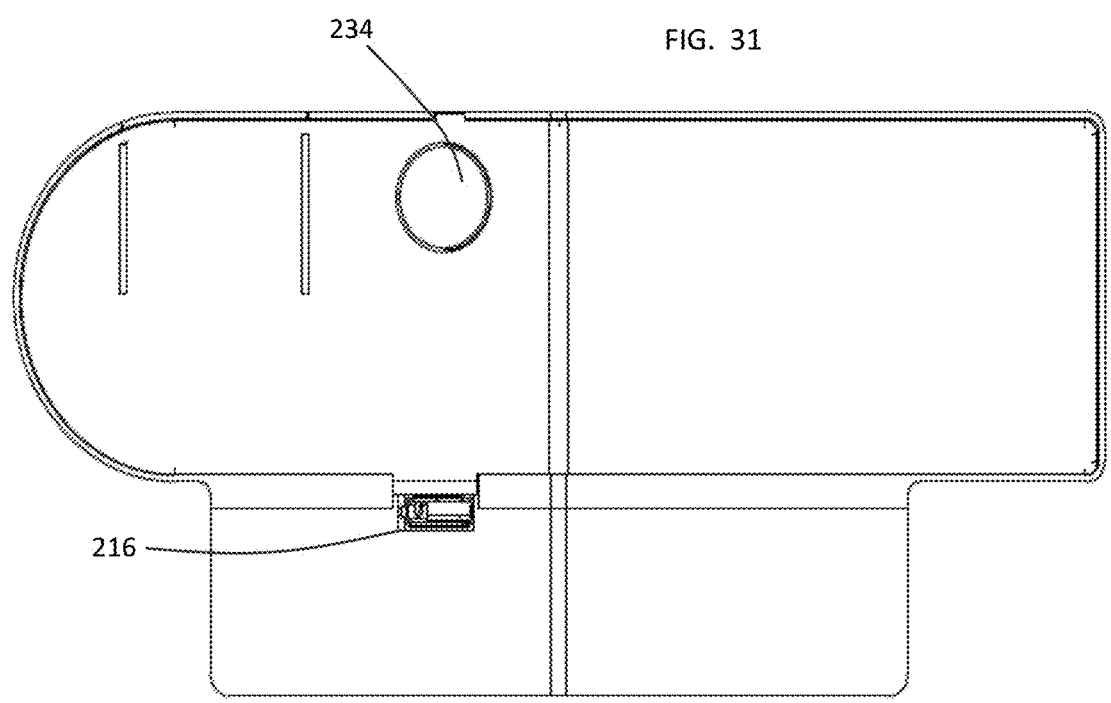

FIG. 32. shows a rear view of enclosure for personal UV device for use with the particulate mask of FIGS. 24-26.

Figure 33:
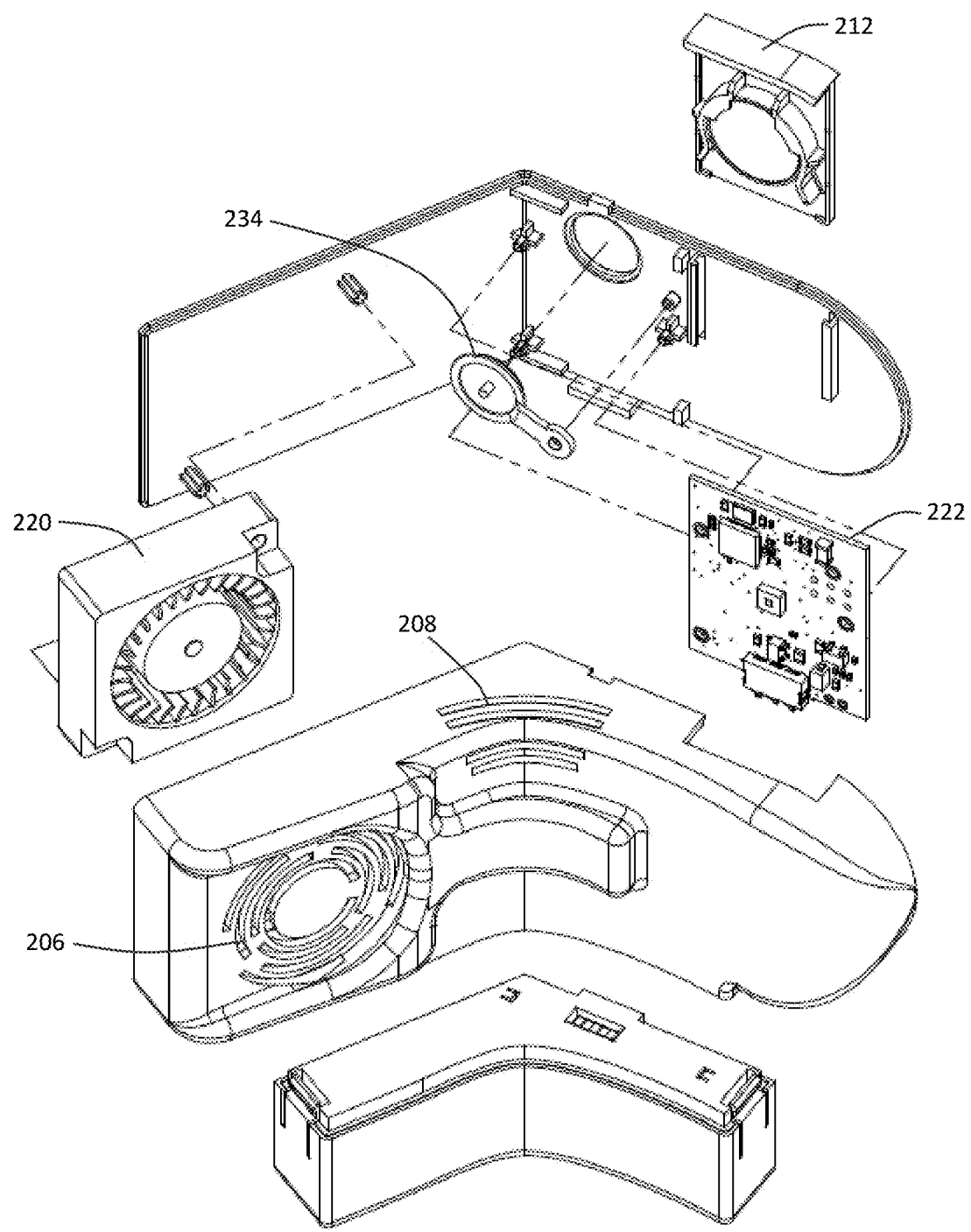

FIG. 33. shows an exploded perspective front view of personal UV device for use with the particulate mask of FIGS. 24-26.

Figure 34:
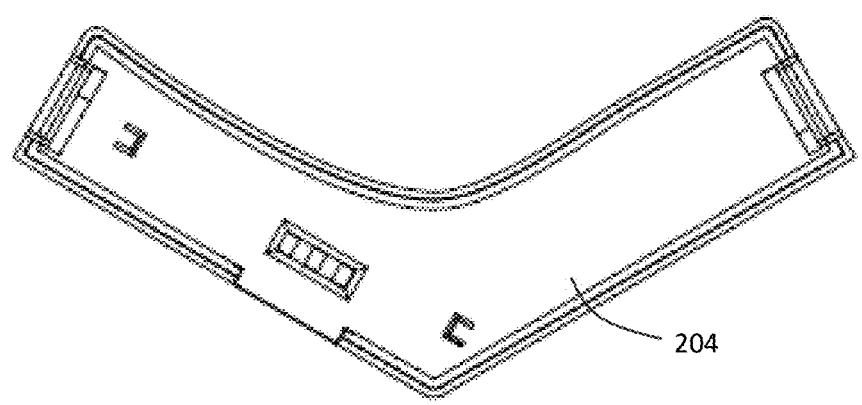

FIG. 34. show side views of the enclosure for a personal UV device for use with the particulate mask of FIGS. 24-26.

Figure 35:
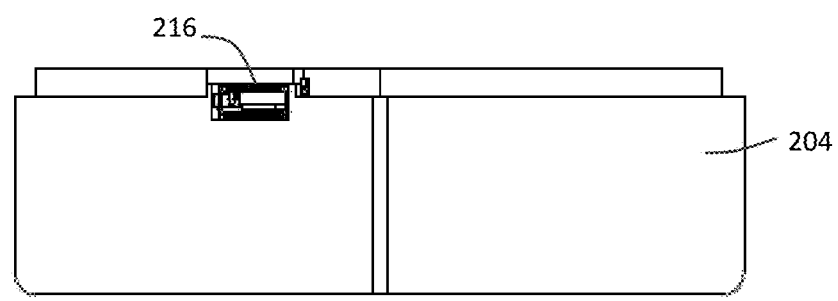

FIG. 35. show side views of the enclosure for a personal UV device for use with the particulate mask of FIGS. 24-26.

Figure 36:
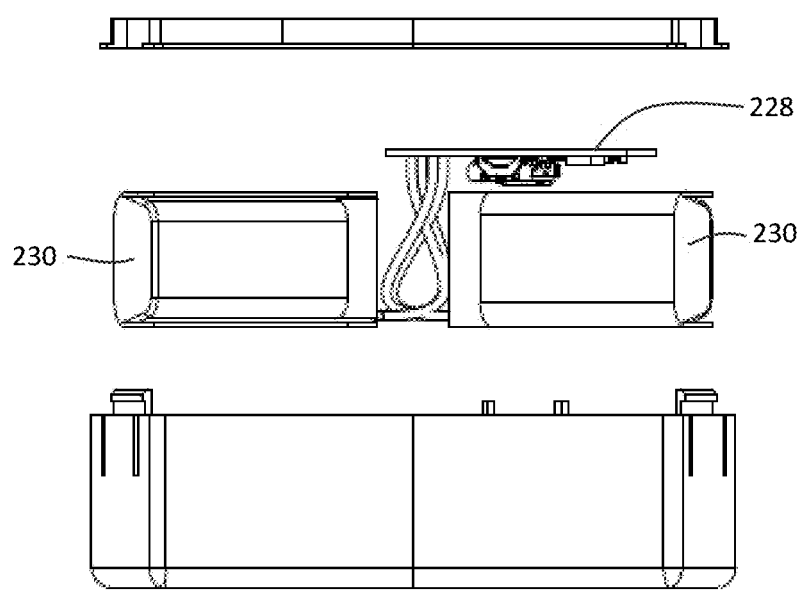

FIG. 36. show side views of the enclosure for a personal UV device for use with the particulate mask of FIGS. 24-26.

Figure 37:
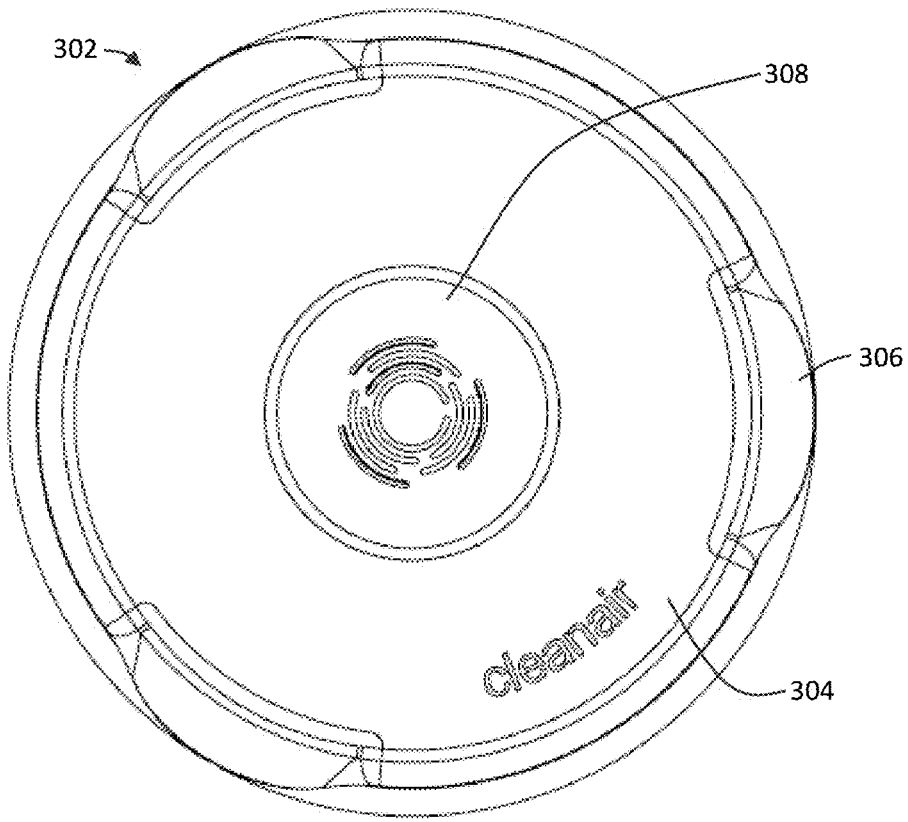
Figure 38:
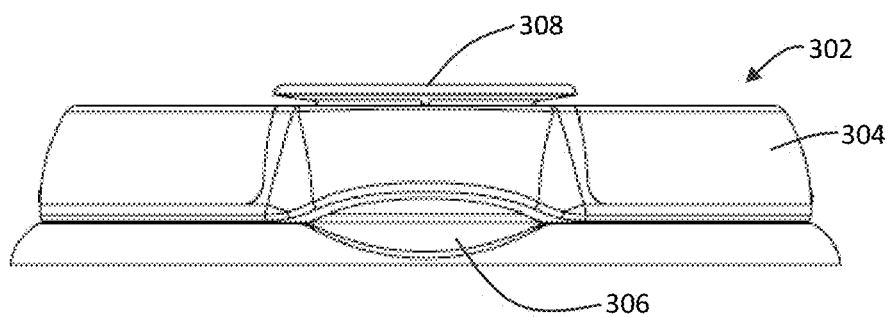
Figure 39:
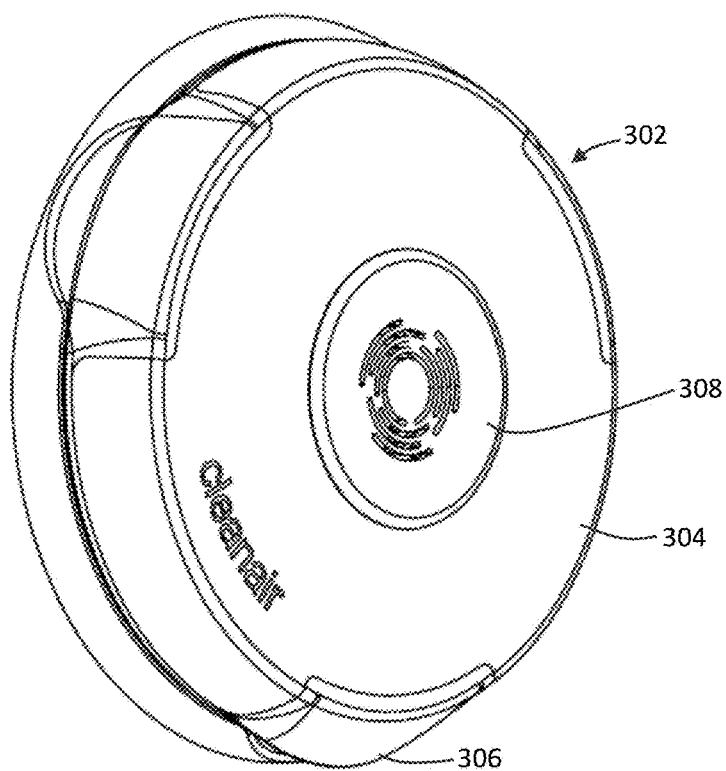

FIG. 37 illustrates a top view of a personal air treatment device according to another embodiment;

FIG. 38 illustrates a side view of the personal air treatment device of FIG. 37;

FIG. 39 illustrates a perspective top view of the personal air treatment device of

Figure 40:
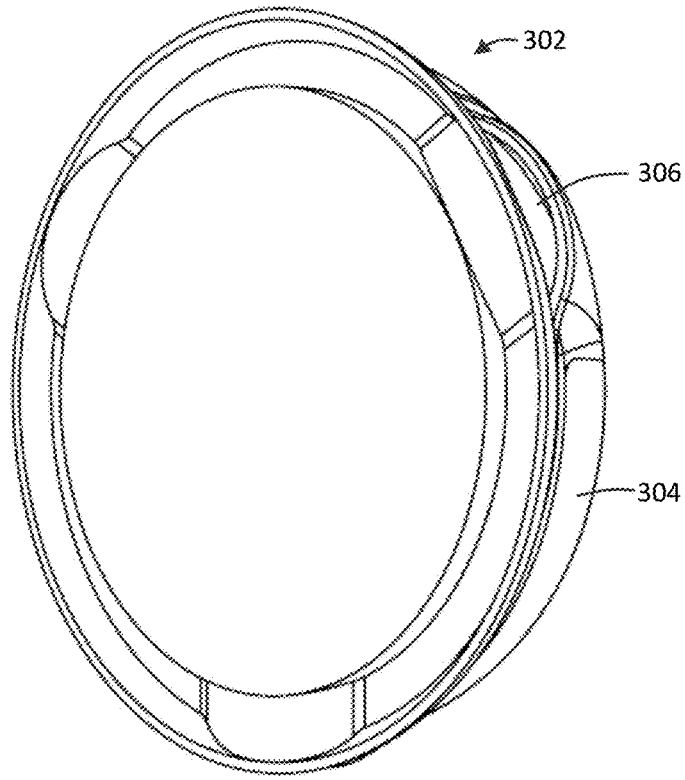
Figure 41:
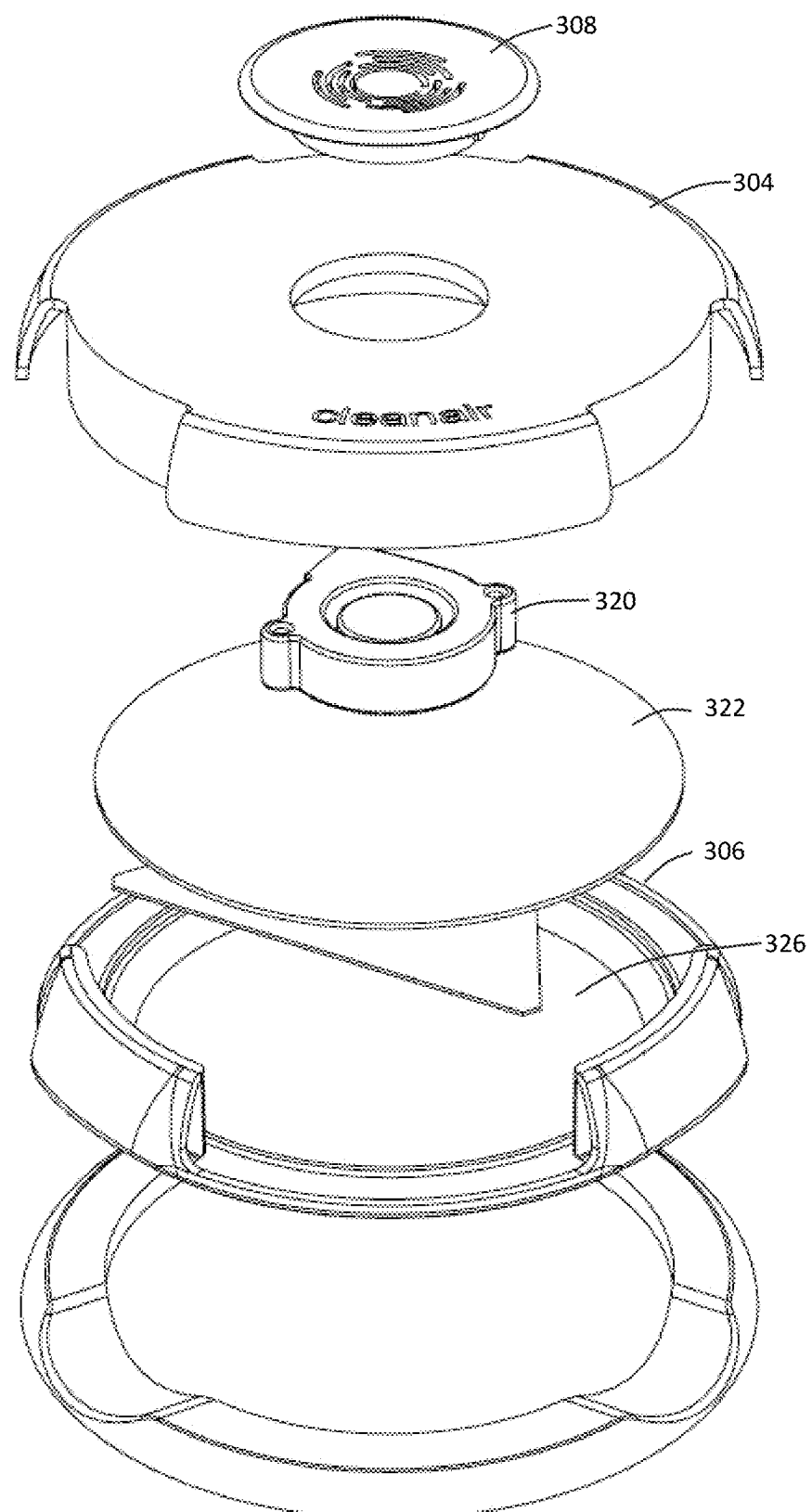

FIG. 37;

FIG. 40 illustrates a perspective bottom view of the personal air treatment device of FIG. 37; and FIG. 41 illustrates an exploded view of the personal air treatment device of FIG. 37.

DETAILED DESCRIPTION

The following description is of exemplary embodiments of the invention only, and is not intended to limit the scope, applicability or configuration of the invention. Rather, the following description is intended to provide a convenient illustration for implementing various embodiments of the invention. As will become apparent, various changes may be made in the function and arrangement of the elements described in these embodiments without departing from the scope of the invention as set forth herein. It should be appreciated that the description herein may be adapted to be employed with alternatively configured devices having different shapes, components, air movers, UV sources and the like and still fall within the scope of the present invention. Thus, the detailed description herein is presented for purposes of illustration only and not of limitation.

Reference in the specification to "one embodiment" or "an embodiment" is intended to indicate that a particular feature, structure, or characteristic described in connection with the embodiment is included in at least an embodiment, implementation or application of the invention. The appearances of the phrase "in one embodiment" or "an embodiment" in various places in the specification are not necessarily all referring to the same embodiment.

With reference now to FIGS. 1-6, a personal air treatment device 2 is shown according to one embodiment of the present invention. Personal air treatment device 2 includes an enclosure or housing 4 enclosing an air impeller 20, air duct 26, UV LED, and a control circuit 22. (See FIG. 9). Housing 4 defines an air inlet 6 and an air outlet 8 and an air pathway 26, duct, or chamber therebetween. A UV LED is disposed along air pathway 26 between inlet 6 and outlet 8 to neutralize pathogens in the air. Housing 4 further includes a scent tray 12 adjacent the air pathway between inlet 6 and outlet 8 to impart a desired scent or other effect to the air. Scent tray 12 may include a scent packet 28. Housing 4 also includes power/status indicator 10, a battery enclosure 14, battery charging/data port 16, and power switch 18.

Figure 1:
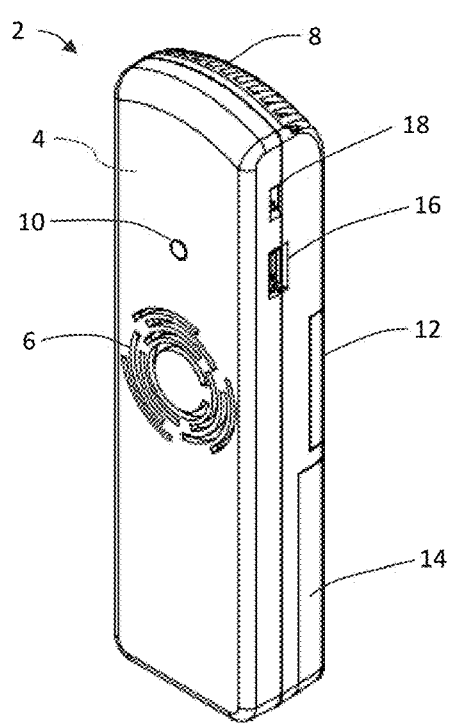
Figure 2:
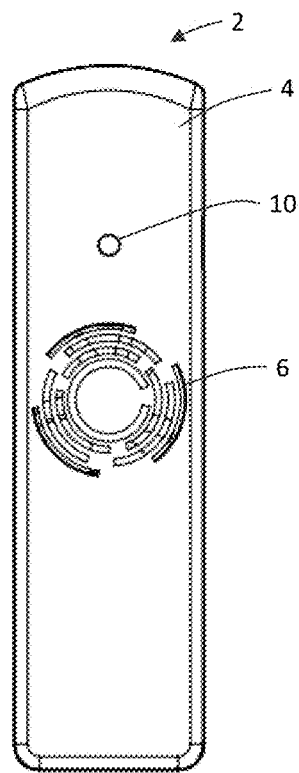
Figure 3:
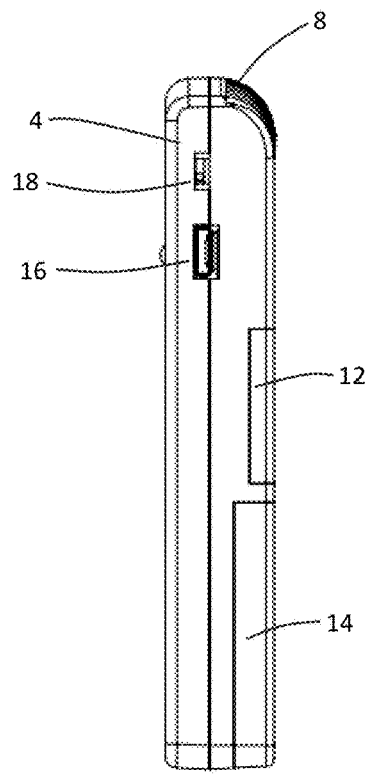
Figure 4:
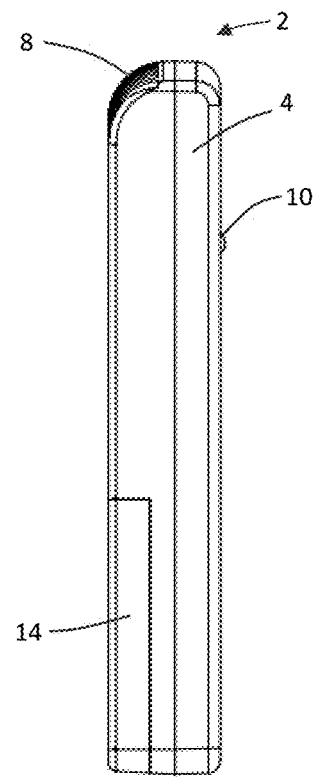
Figure 5:
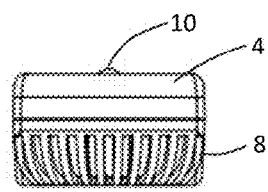
FIG. 5 illustrates a top view of the personal air treatment device of FIG. 1.
Figure 6:
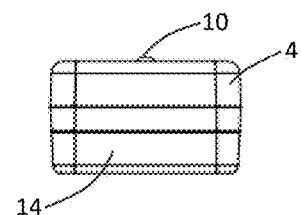
FIG. 6 illustrates a bottom view of the personal air treatment device of FIG. 1.
Figure 7:
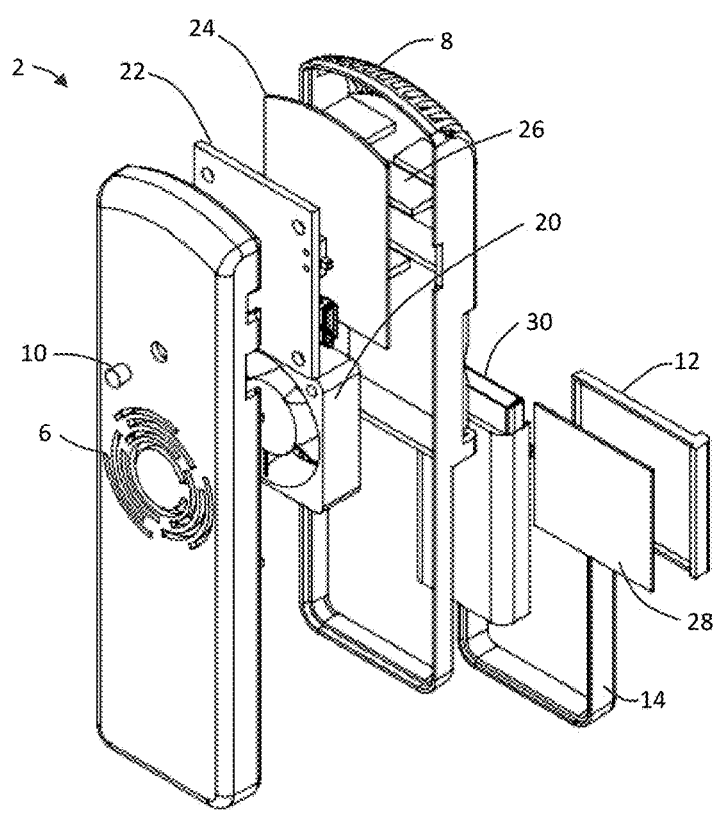
FIG. 7 illustrates a cross-sectional view of the personal air treatment device of FIG. 1.
Figure 9:
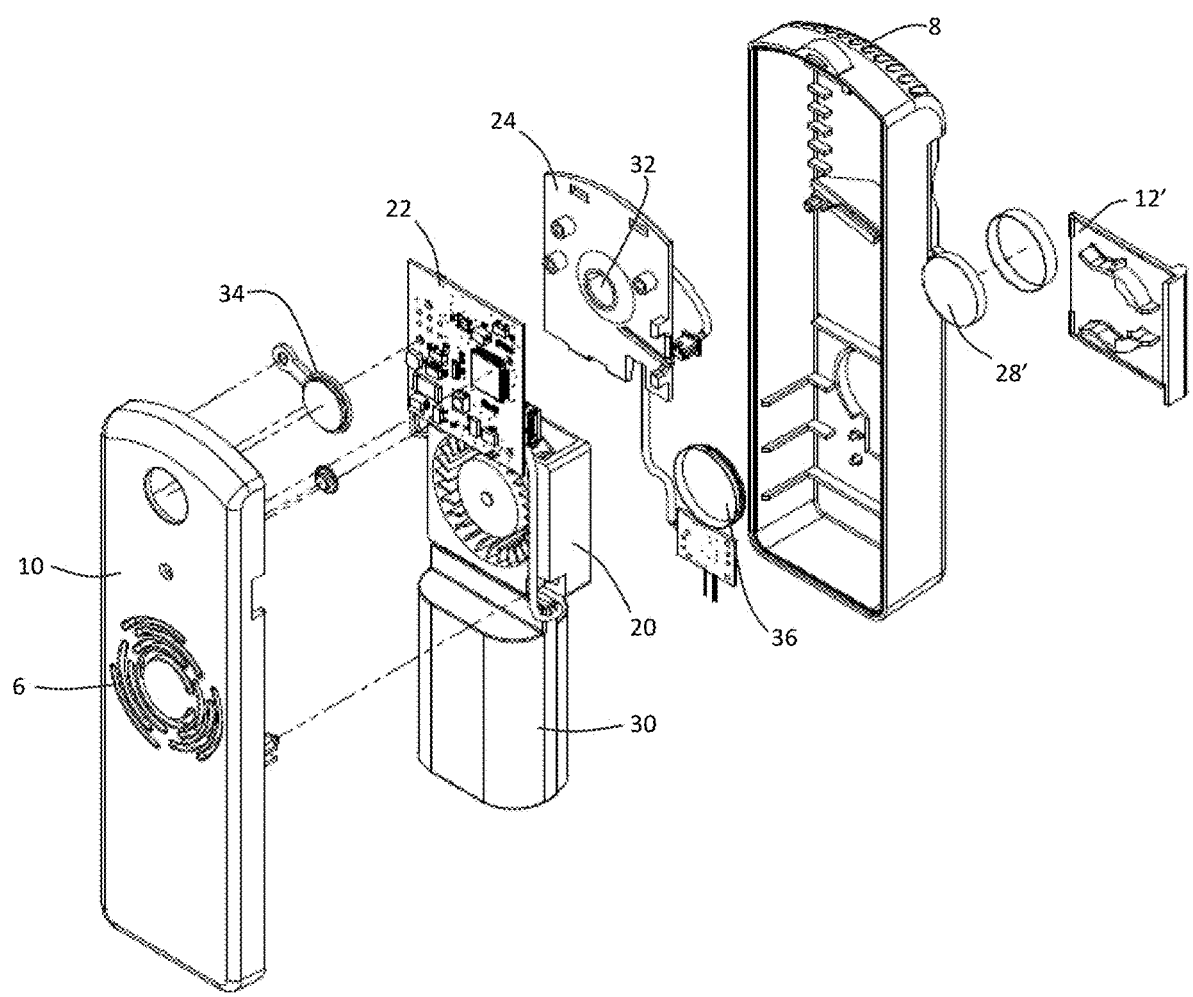
FIG. 9 illustrates a cross-sectional view of the personal air treatment device of FIG. 1.
Figure 10:
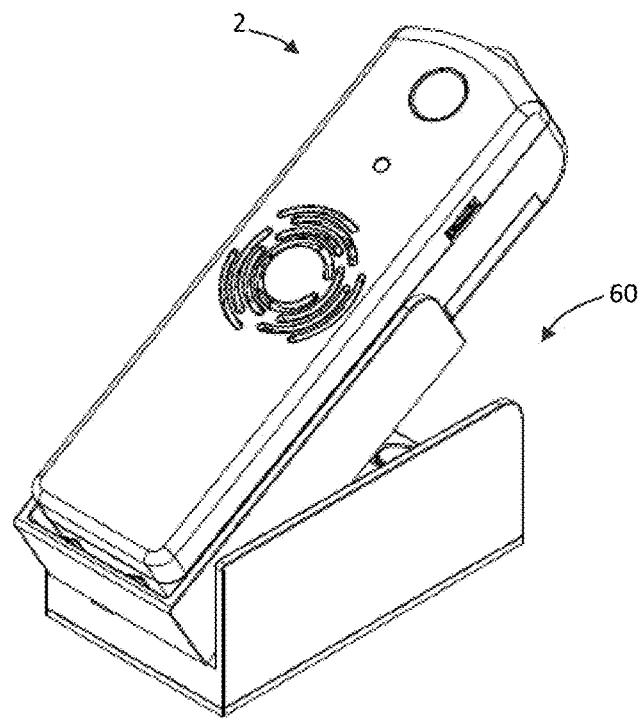
FIG. 10 illustrates a perspective view of a personal air treatment device docked in a charging cradle.
Figure 11:
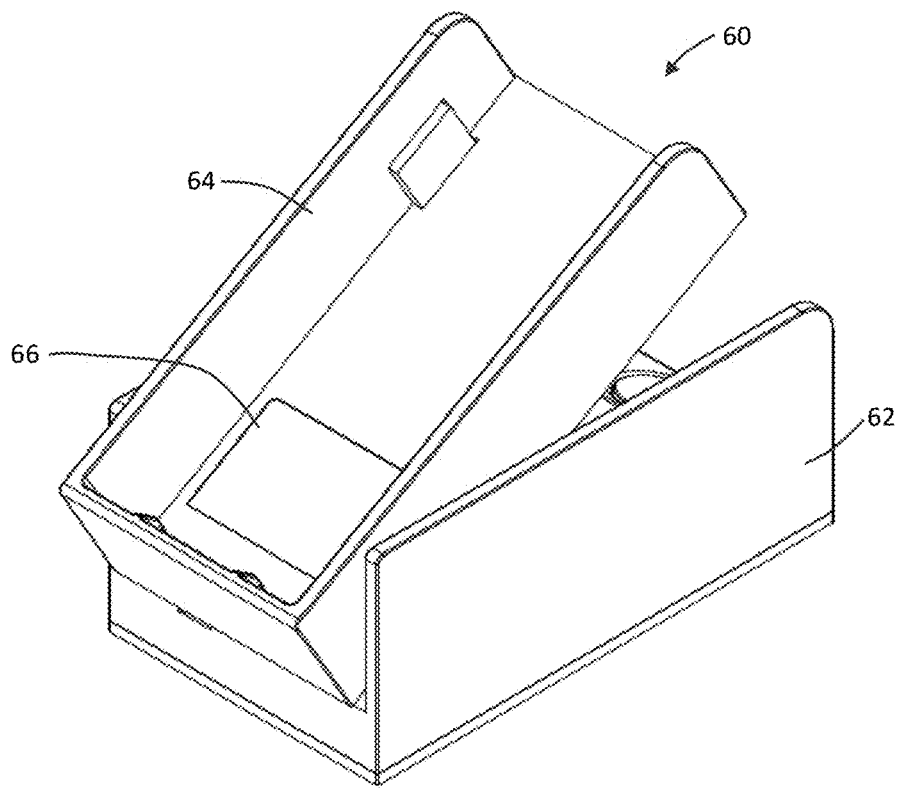
FIG. 11 illustrates a perspective view of the charging cradle of FIG. 10.
Figure 12:
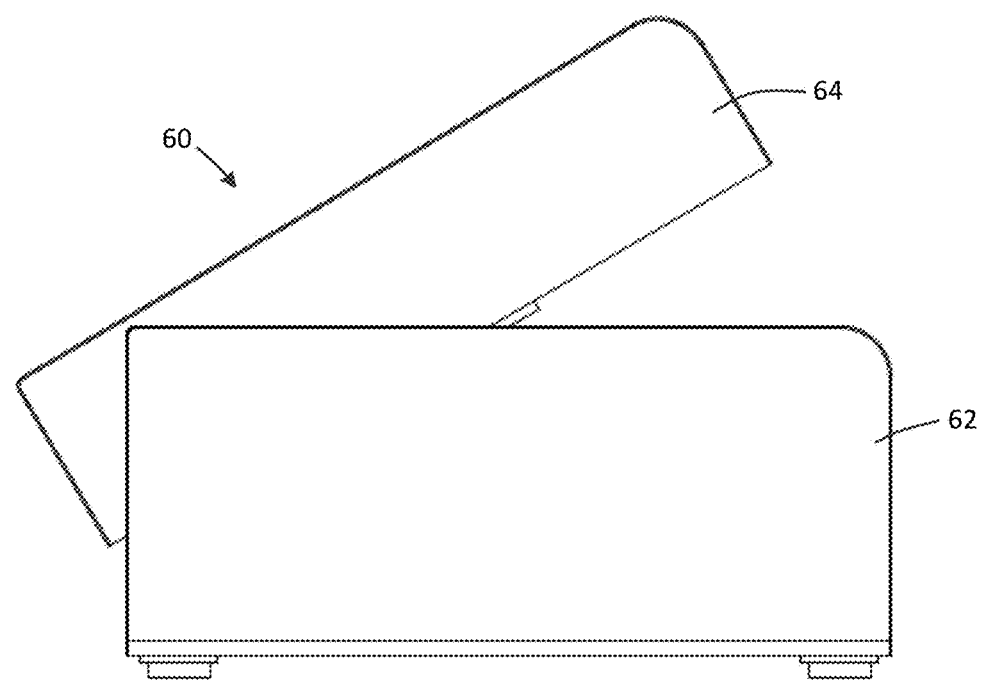
FIG. 12 illustrates a side view of the charging cradle of FIG. 10.

With reference now to FIGS. 7 and 9, embodiments of personal air treatment device 2 are illustrated in exploded views. Personal air treatment device 2 includes control circuit board 22 for controlling operations of air impeller 20, the UV LED, and wireless connectivity hardware. A recharge able/removable battery 30 is disposed within the battery enclosure 14 to power the air impeller 20, UV LED, and control circuits.

A reflective surface/UV shield 24 is provided adjacent air pathway 26 to reflect the UV throughout air pathway 26 and prevent escape of UV beyond air pathway 26. A removable scent package insert 28, 28' is received within insert tray 12 allowing for user selection of any number of air additives, e.g., oils, essences, fragrances, and the like. In some embodiments, scent package insert 28, 28' comprises an aroma reservoir, e.g., an essential oil pellet, configured to entrain scents in the air in the pathway. In some embodiments, scent package insert 28, 28' comprises a filter such as a HEPA filter, gauze or the like. Various aromatics can be added to the filter to provide for evaporation of oils or other additives positioned along or across pathway 26. Release of the additives can be enhanced by heating, e.g., by resistive heating or by positioning near a heat source associated with the control circuit or power supply.

During the operation of the personal air treatment device, air is drawn into inlet 6 and is conveyed by air impeller 20 along a circuitous pathway 26 toward outlet 8. Pathway 26 is configured to afford sufficient dwell time or UV exposure to substantially inactivate any airborne pathogens conveyed through pathway 26.

Figure 8:
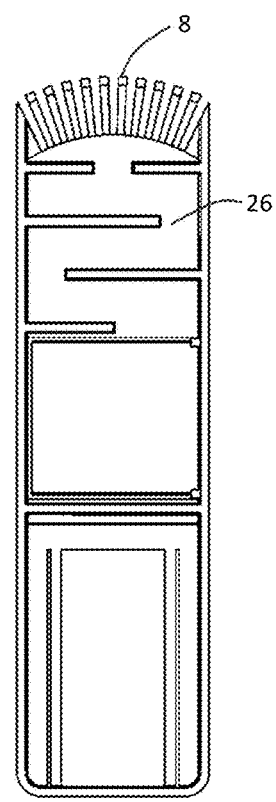
FIG. 8 illustrates a cross-sectional view of the personal air treatment device of FIG. 1; showing the UV LED.

With reference to FIG. 8, a cross-sectional view of housing 4 illustrates outlet 8, pathway 26, slide insert 12, and battery enclosure 14. In some embodiments, housing 4 is formed by injection molding or additive printing. In some embodiments, pathway 26 is formed integral with sidewalls of housing 4. In some embodiments, pathway 26 forms a maze-like duct or a spiraled duct insert.

With reference now to FIG. 9, personal air treatment device 2 is shown with UV LED disposed on the rear of circuit board 22 and positioned to align with aperture 32 to irradiate air pathway 26. UV LED can be powered and controlled to achieve any desired irradiation cycle time or effect. For example, the circuit board and power supply can be configured such that UV LED is powered for a predetermined amount of time after activating power button 34 or according to a schedule. Similarly, the UV LED can be powered in response to movement, user input, and the like. In some embodiments, operation of the UV LED and air impeller is coordinated with other personal air treatment devices in the vicinity, e.g., via Bluetooth or other wireless connectivity. Thus, multiple personal air treatment devices may be controlled to achieve a combined effect.

With reference to FIGS. 10-14, a personal air treatment device 2 is shown docked in a charging cradle 60. Charging cradle 60 includes a base 62, cradle 64, and near-field charger region 66. Cradle 62 is movable relative to base 62 between a stowed position and a deployed position and may be positioned therebetween.

Figure 13:
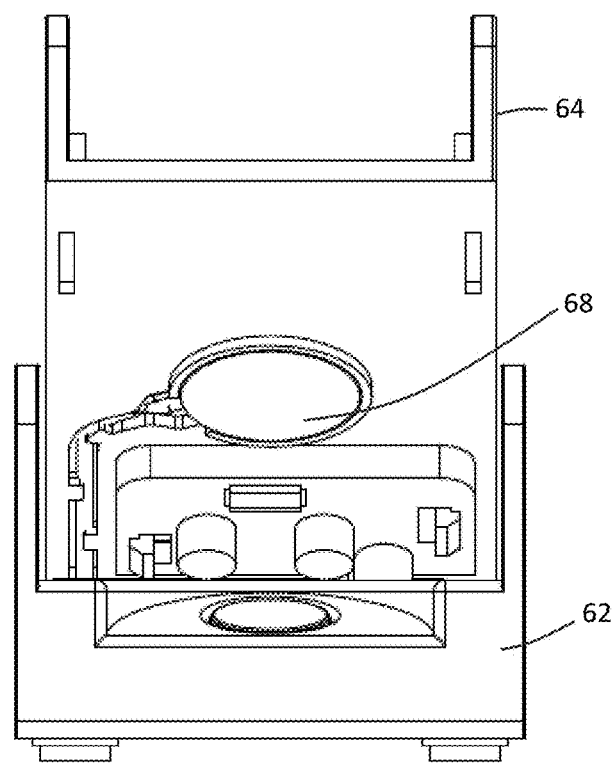
FIG. 13 illustrates a rear view of the charging cradle of FIG. 10.
Figure 14:
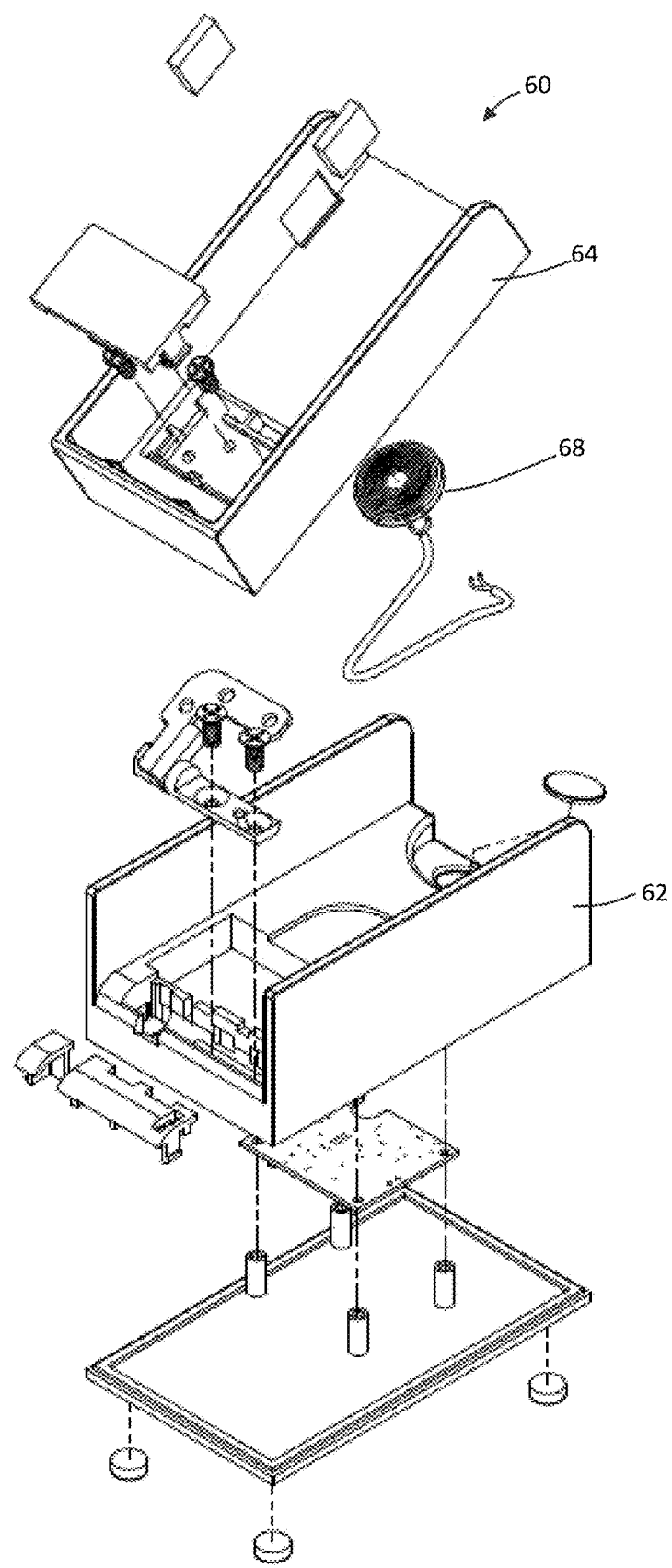
FIG. 14 illustrates an exploded perspective view of the charging cradle of FIG. 10.

With reference to FIGS. 13-14, charging cradle 60 includes a near-field charging coil 68 adjacent near-field charger region 66. Charging coil 68 is controlled by charging circuit 72 disposed within base 62. Cradle 64 is movable relative to base 62 via a hinge.

Figure 15:
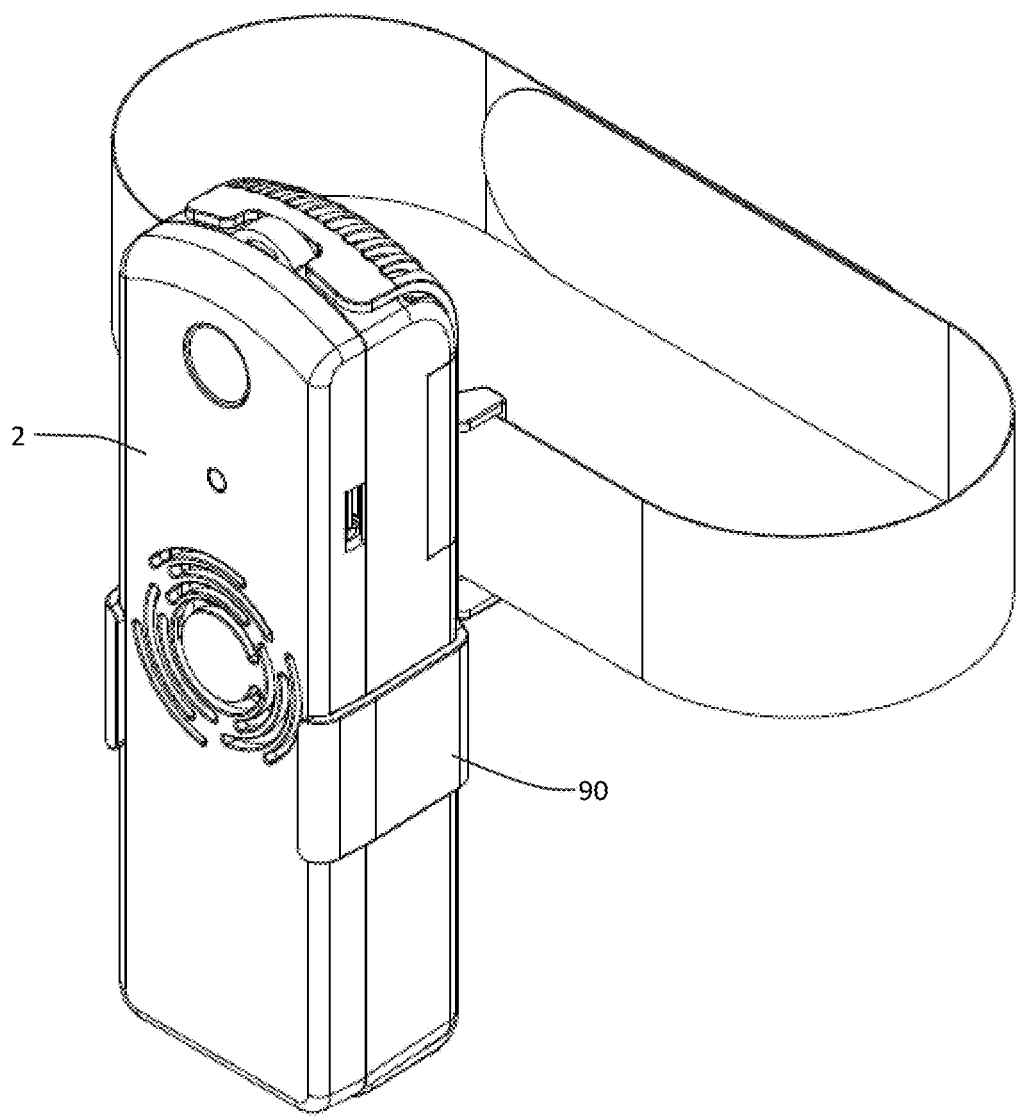
FIG. 15 illustrates a personal air treatment device secured in an arm-band cradle.
Figure 16:
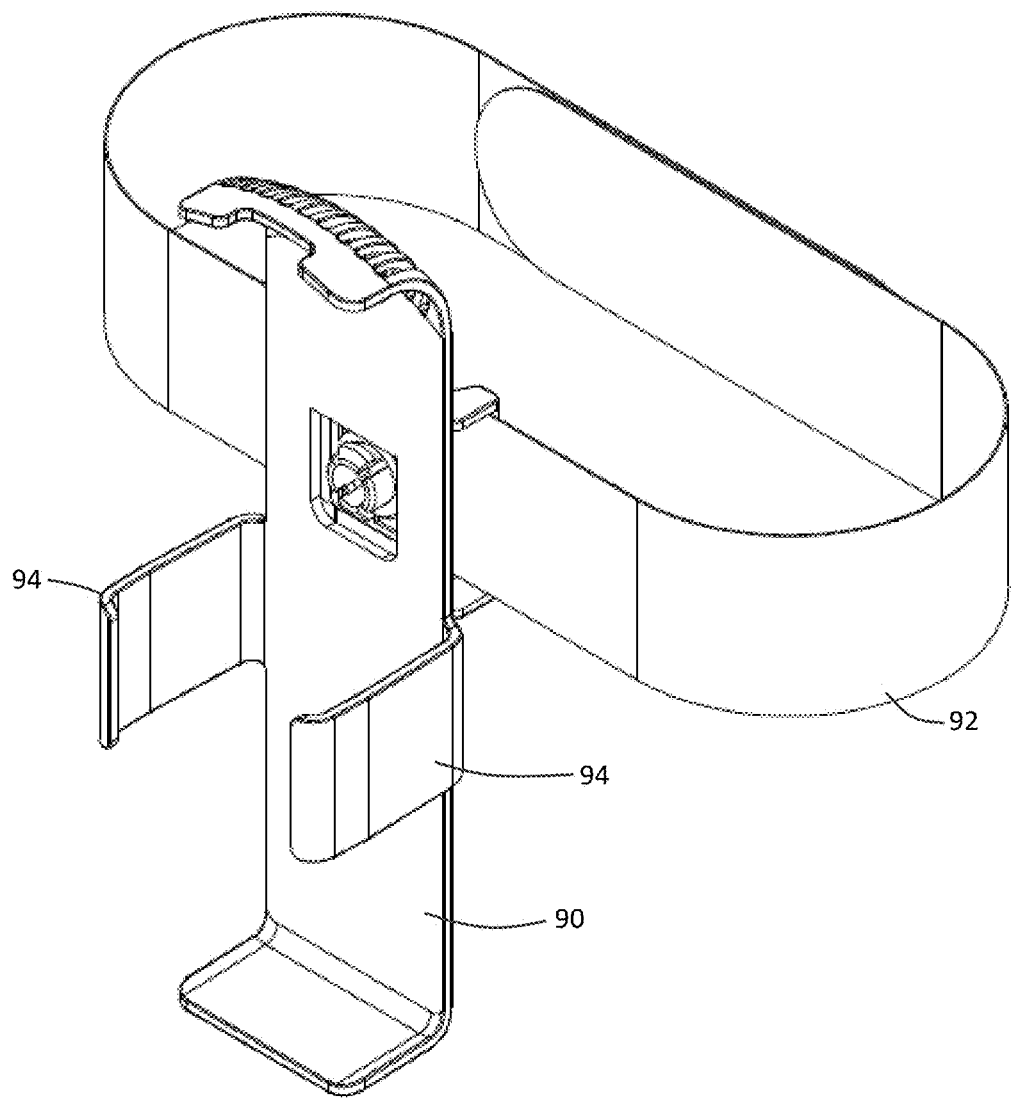
FIG. 16 illustrates a perspective view of the arm-band cradle of FIG. 15.
Figure 17:
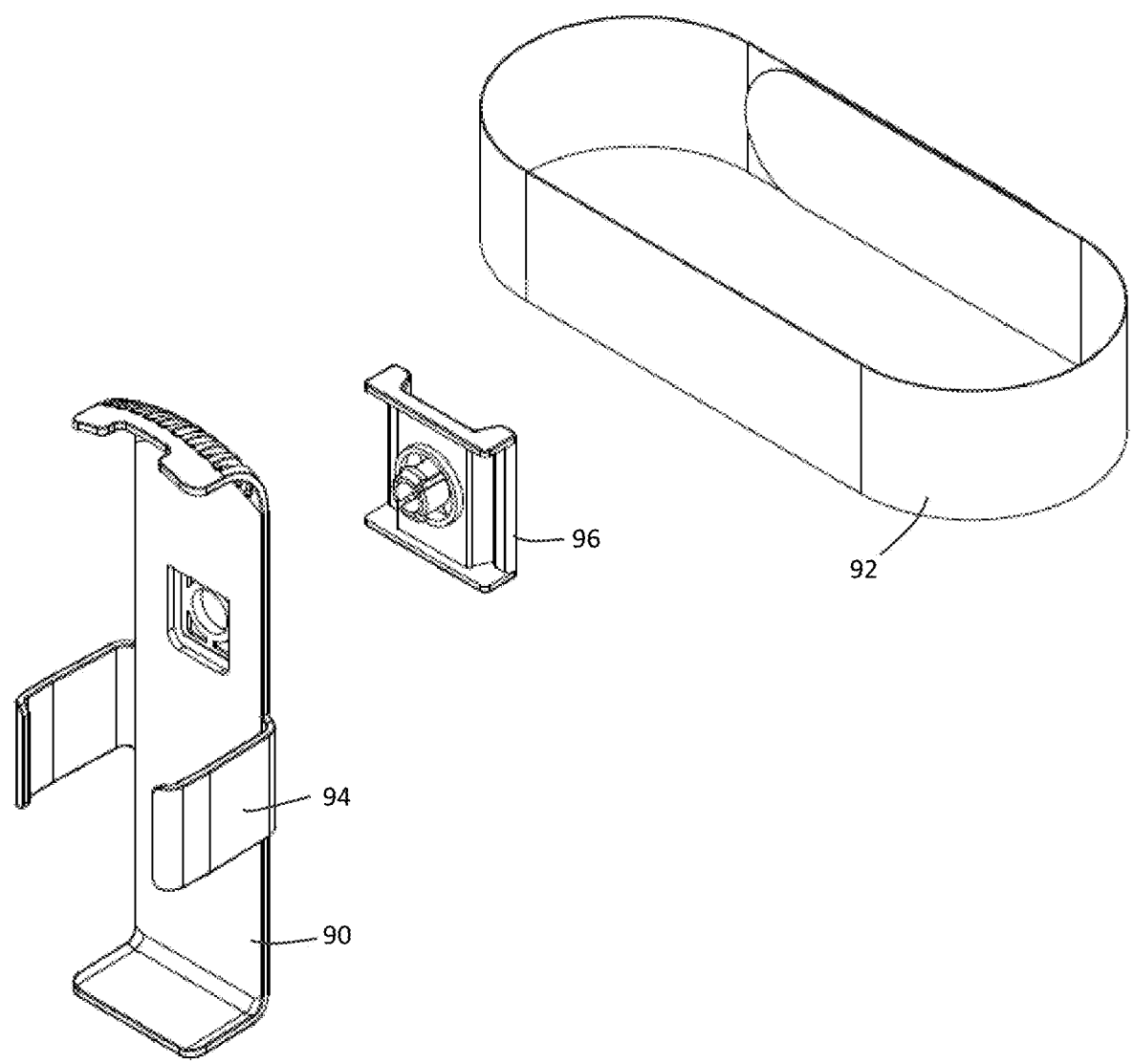
FIG. 17 illustrates an exploded view of the arm-band cradle of FIG. 15.
Figure 18:
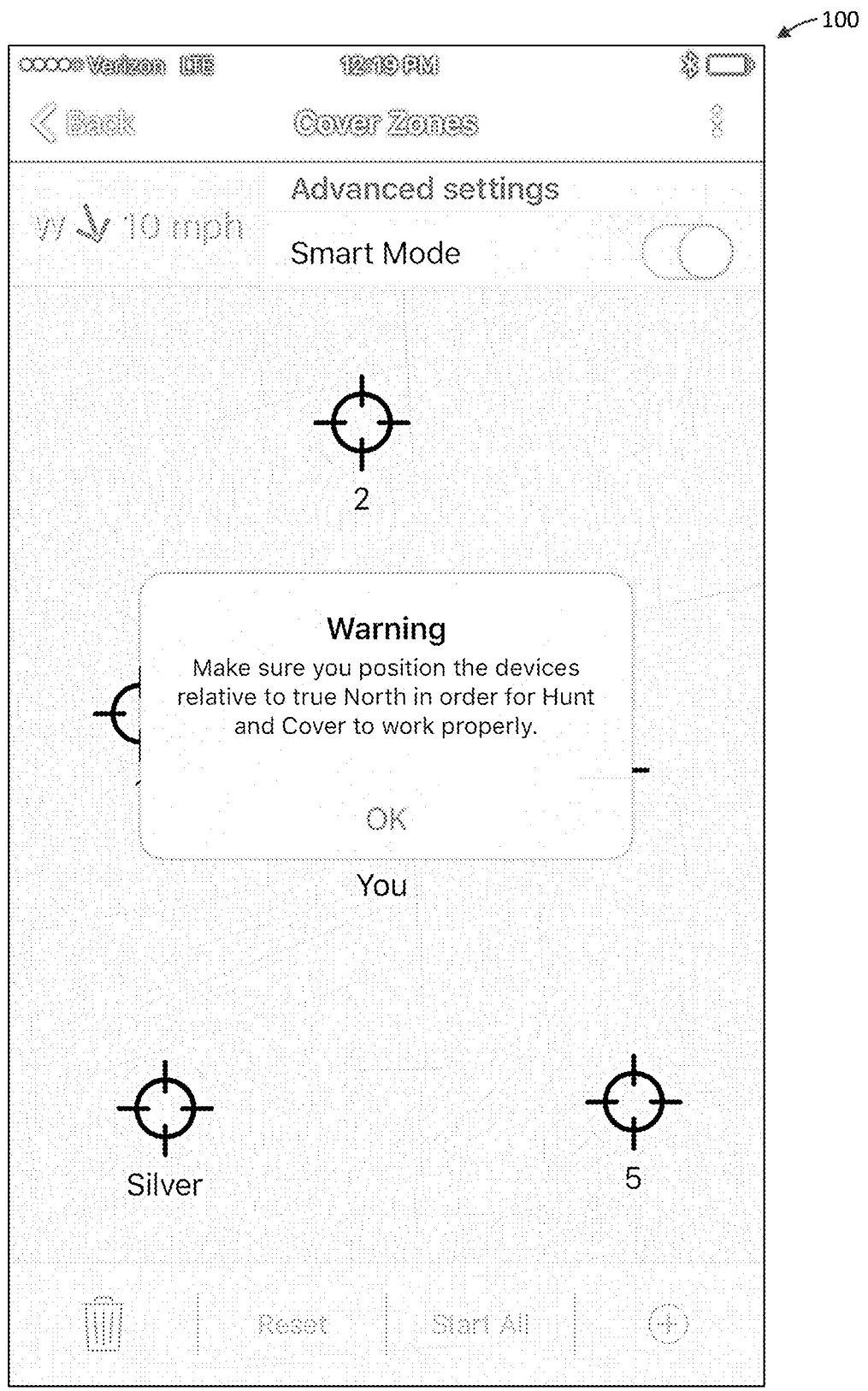
FIG. 18 illustrates a screenshot of an application for remotely controlling multiple personal air treatment devices.

With reference to FIGS. 15-17, a personal air treatment device 2 is shown secured in an arm-band cradle 90. Arm band cradle 90 includes one or more cradle clips 94 configured to secure personal device 2 within the cradle 90. An arm band 92 passes through bracket 96 secured to cradle 90.

Any number of brackets, cradles, and other accessories may be used with the personal air treatment device. For example, positioning devices may be configured to engage a stroller bar, vehicle air vent, cigarette lighter socket, arm band, lanyard and the like, to suitable position the air treatment device relative to a user.

With reference to FIGS. 18-23, screenshot illustrate features of an application for remotely controlling multiple personal air treatment devices in the context of scenting/masking dispersion for hunting.

Figure 19:
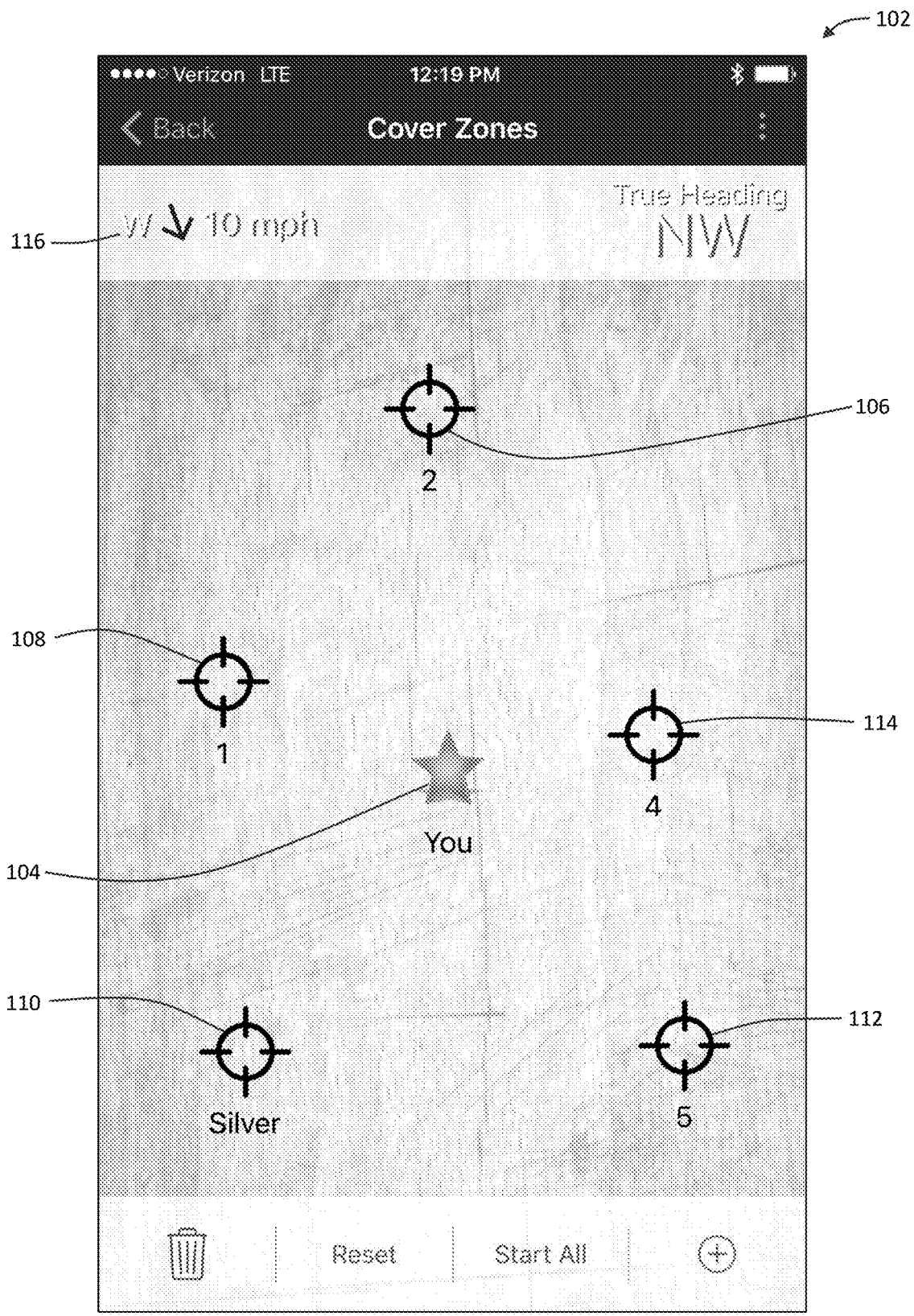
FIG. 19 illustrates a screenshot of an application for user initiated control of multiple personal air treatment devices positioned remote from the user.

With reference to FIG. 19, in some embodiments, the personal air treatment devices are remotely controllable, e.g., via a smartphone application over Bluetooth or Wi-Fi connections. The application may be used to help optimize positioning of the air treatment devices around the user, for example, during use in masking or dispersing scents during hunting. For example, wind patterns, temperature, topography, and any number of other types of data may be used to inform recommended positioning and other settings for any number of air treatment devices. Device positioning may be altered based on any number of factors or considerations, including type of game being hunted, number of devices in use, density of trees or brush, number of hunters, and the like.

Figure 20:
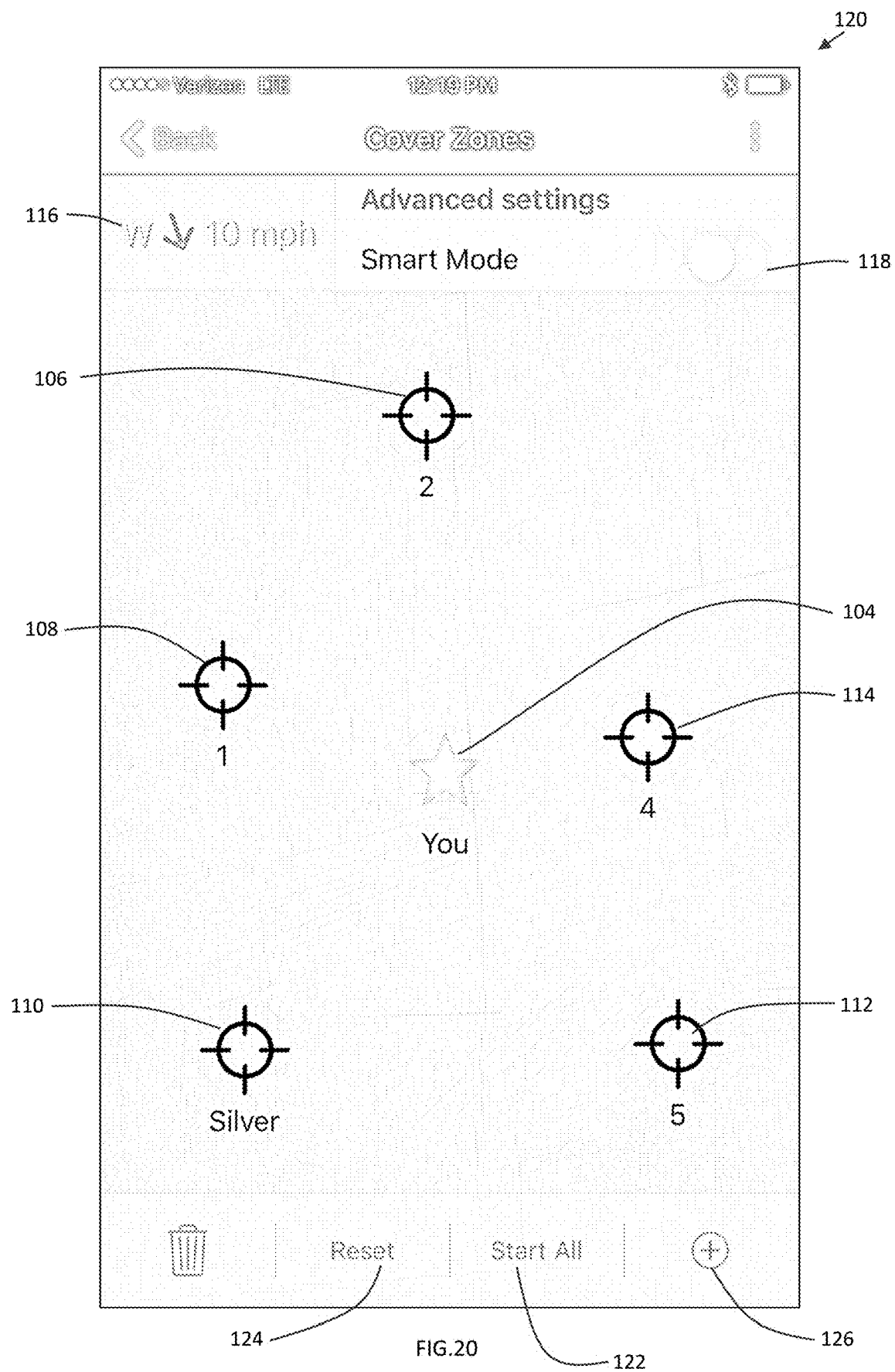
FIG. 20 illustrates a screenshot of an application for automatically controlling multiple personal air treatment devices positioned remote from the user.

With reference to FIGS. 19-20, the position of devices 106-114 is shown on screen relative to a hunter "You." A wind indicator 116 shows the direction and magnitude of the local wind patterns. Local wind data may be obtained over the internet from real-time public weather databases. Alternatively, in some cases, the wind data may be accessed using geolocation as well as local communication use BLE to another device in the proximity to obtain accurate data without relying on public weather databases.

The user can configure settings for individual devices or groups of devices. For example, the user may choose to activate, idle, hibernate, one or more devices at a time, e.g., start all, stop all, reset all, and the like. The user may tap individual devices or region containing devices to update settings, e.g. Power, dispersion levels, wind direction-dependency and the like. In some embodiments, user application features may enable video recording or time lapse photography. Add device feature 128 allows a user to add any number of devices to the application interface. A Reset feature 124 allows the user to reset the settings for any number of devices. Start All feature 126 allows the user to restart any number of selected devices.

In some applications, a "Smart Mode" feature 118 enables pre programmed settings or operations of devices 106-114. For example, Smart Mode 118 can operate one or more of the devices in a preprogrammed mode, e.g., according to a scheduled program, timed setting, rotation, wind-based algorithm, and the like.

Figure 21:
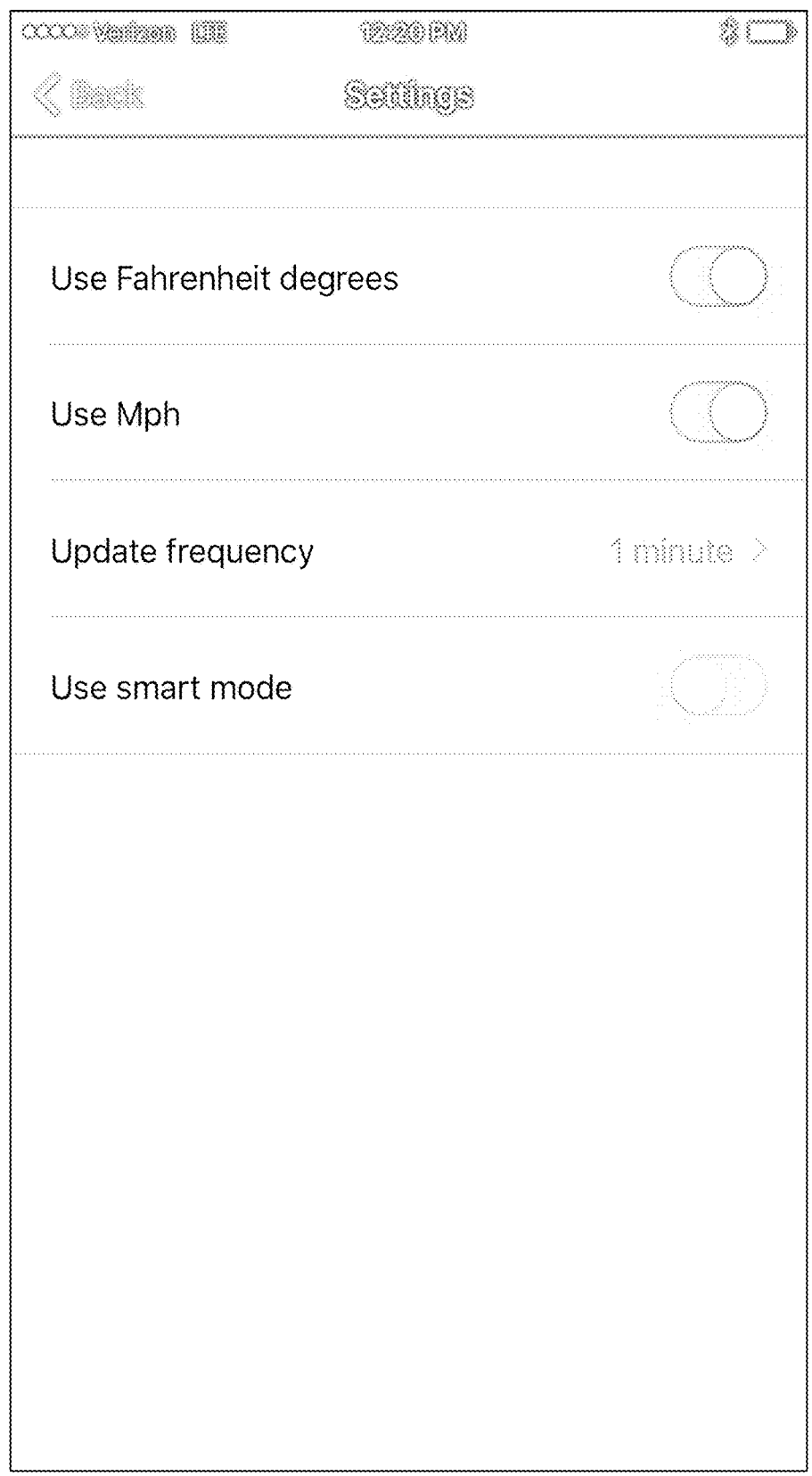
FIG. 21 illustrates a screenshot of a settings page for an application for automatically controlling multiple personal air treatment devices positioned remote from the user.

With reference to FIG. 21, a Settings page screenshot 130 shows some of the user settings available, including temperature units, wind speed units, device data update frequency, and Smart Mode toggle. The settings allow addition of features in new versions based on new rules and new data.

Figure 22:
FIG. 22 illustrates a screenshot of a weather tracking feature of an application for controlling multiple personal air treatment devices positioned remote from the user.

With reference to FIG. 22, screenshot of a weather tracking feature 140 shows hourly and weekly local weather data, e.g., precipitation, wind, cloud cover, and the like. Data from central weather databases, local weather stations, portable weather sensors and the like can be share among application users within a relevant region.

Figure 23:
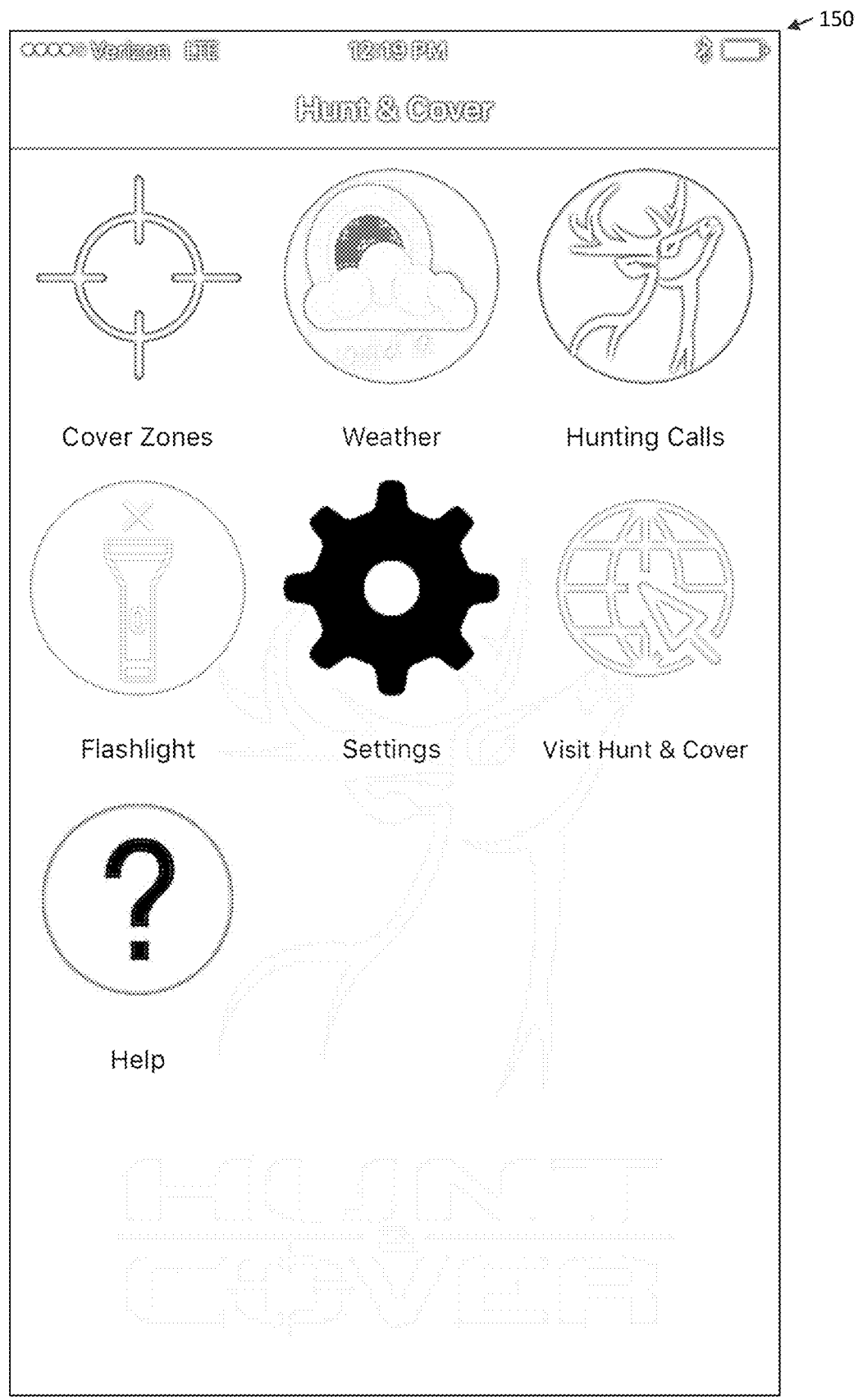
FIG. 23 illustrates a screenshot of a features selection screen of an application for controlling multiple personal air treatment devices positioned remote from the user.

With reference to FIG. 23, a screenshot shows a user interface application features page 150. Features may include "Cover Zones", "Weather", "Hunting Calls" "Flashlight", "Settings", "Website", and "Help" features. The Cover Zones feature allows the user to establish different zones and assign various devices to the different zones. Zones and device groupings may be assigned different settings, schedules, and the like. The Weather feature allows the user to track local weather and to receive updates useful to inform device settings.

The Hunting Calls features page 160 allows a user to select relevant animal calls to help draw in the selected animal, in conjunction with the scenting feature of the device. The sounds may be played on the smartphone and/or by any number of the air treatment devices.

The Settings feature saves the specific features of the application for the user such as Fahrenheit or Celsius, Kilometers to Miles per hour (MPH) for wind, etc.

The Website feature allows the user to visit the specific page relevant to ordering more items or gathering information about new features. The Help feature provides general information on how the application works. It can also have on boarding features as well. The Flashlight feature offers basic flash-on features on the smartphone.

In some embodiments, the air treatment device is controllable using Bluetooth protocols, e.g., to remotely turn off/on the scent dispersion and cover up of a device.

In some embodiments, the application tracks GPS coordinates of the device during use and logs of device usage data, such as length of time used, the number of devices controlled and how long each runs. In some embodiments, the GPS coordinate and/or local wind speed and direction data are used to "intelligently" turn off/on the respective devices based on the wind direction. For example, if the wind is blowing 3 mph NE, the smart application turns on downwind units A and D. If the wind shifts as the application automatically adjusts to turn off units A and D turn on units B and C. Devices may be assigned different purposes, e.g., a "cover" purpose or a "scenting" purpose, and may be managed by the Smart Mode feature of the application of by the individual user.

The application can be used to control any number of devices, e.g., 1-32. Devices can be turned off/on based with a simple touch of a check box. The application may cycle the devices, e.g., turned off/on in <1 sec cycles over a scheduled period.

The user can organize the devices on screen to correspond with physical device locations relative to the user, e.g., use the + symbol on the screen and dragging the new device to the desired location on the screen. Using Goggle Maps, the application can overlay the satellite image and device icon to indicate precise positioning. Similarly, devices can be removed from the system by simply dragging the respective icon to a trash-can on-screen.

The Reset feature puts the devices back in a "default" position and mode. For example, in some cases, the default mode places the Hunter user is in the middle of the devices with the surrounding devices positioned, e.g., 12, 3, 6 and 9 o'clock respectively.

In some embodiments, data logging allows for tracking of how long the user is running the application and various devices. This logged data may be aggregated, anodized, and used for bench marking purposes. For example, data collected can include MAC address, cell, location, date, time and the like.

This data can be used, in combination with retail beacon technology to offer in-app promotions. For example, when the user walks into a sporting goods store the application can offer pop up alert showing a special coupon based on specific criteria that a partner seeks to promote. In another example, the application data may be aggregated to determine how many users "pass" or "stop-by" a particular product or retail location. This can useful, for example, to display a special alert if user is standing in front of Product X for longer than 1 minute.

In some embodiments, intermittent operation prolongs scent reservoir life and battery life. For example, scenting may continue for 3-5 hours with selective operation in contrast to 1-2 hour duration of common passive scenting systems.

With reference to FIGS. 25-26, in some embodiments, a personal air treatment device 202 may be integrated with a personal particulate mask 200. The personal air treatment device 202 may be integrated, yet be removable, e.g., to change a battery, filter, scent packet insert, and the like. In some embodiments, the device is integrated within the nose region of mask 200. In other embodiments, the device is coupled to a central inlet valve of particulate mask 200 or integrated along an edge of mask 200. Suitable particulate masks include N95 type masks and the 'N95' designation means that the respirator blocks 95% of small (0.3 micron) test particles during testing. If properly fitted, the filtration capabilities of N95 respirators exceed those of typical face masks. However, even a properly fitted N95 respirator does not eliminate the risk of illness from various sources. Suitable examples of N95 mask include the "Affinity Foldable Respirator" available from MRSA and the "Particulate Respirator" available from 3M.

The particulate mask and personal UV air treatment device together serve to both filter and UV irradiate the air entering the mask. In some embodiments, the personal UV air treatment device operates continuously to create a positive pressure within the particulate mask. In some embodiments, the UV air treatment device operates intermittently, e.g., in response to negative pressure or airflow during breathing by the wearer. In some embodiments, the unit can fit on to almost any mask and disperse essential oil into the breath space to enhance air quality, e.g., by masking unpleasant odors. The integral particulate mask and air treatment devices are particular useful in congested city centers, airports, health care facilities, and the like.

With reference to FIGS. 27-36, components of personal air treatment device 202 are shown for use with particulate mask 200. Housing 204 defines a concave enclosure configured to fit within the nose region of mask 200. Housing 204 may include a nose-bridge portion 210. Inlet 206 and outlet 208 serve to conduct air within the mask through device 202.

Figure 27:
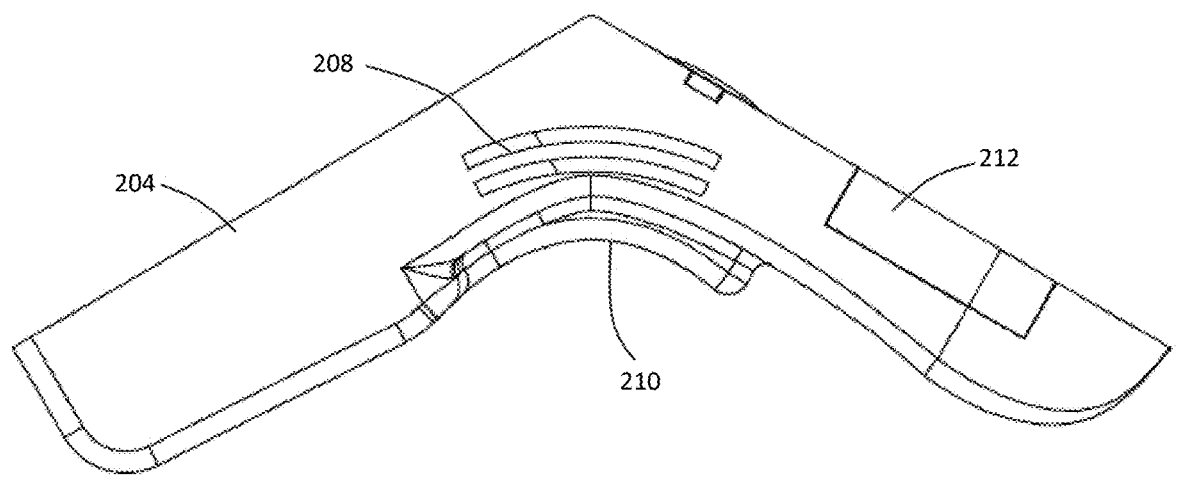
FIGS. 27-28 show side views of an enclosure for a personal UV device for use with the particulate mask of FIGS. 24-26.
Figure 28:
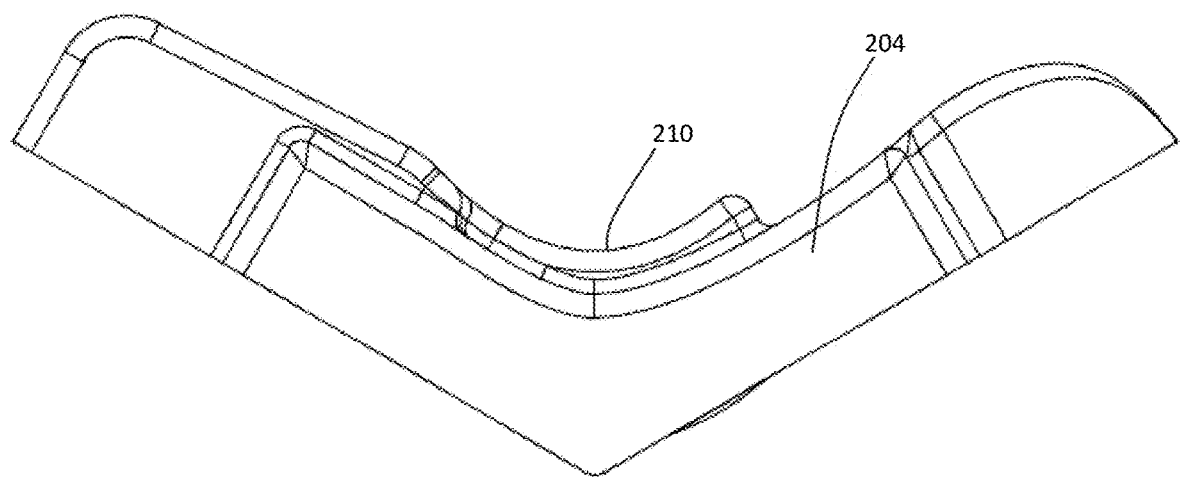

FIGS. 27-28 show side views of an enclosure 204 for personal UV device 202 for use with the particulate mask of FIGS. 24-26. FIG. 27 is the top view showing where air is expelled through the outlet channels. The top right shows removable tray 212 where the refillable scent packet insert 228 sits. The essential oil cartridge/scent packet insert 228 is removable and the wearer can choose to use essential oil or no oil.

FIG. 29. Shows a front view of enclosure 204 for a personal UV device for use with particulate mask 200 of FIGS. 24-26. Enclosure 204 defines air inlets 206 through which air enters UV device 202. FIG. 29 shows the left chamber pulling air in while the chamber is recessed to prevent blockage of the air inlet by the cheek of the user. The middle section defines outlet slots 208 that allow air to be released adjacent the nose of the wearer. A middle channel may be raised to allow air to flow naturally and to keep the majority of the surface away from the wearer.

FIG. 30. Shows a top view of enclosure 204 for personal UV device 202 for use with the particulate mask of FIGS. 24-26. UV device 202 includes a charge receptacle 216 for charging the battery, and includes an on/off button 234.

FIG. 31. Shows a front perspective view of enclosure 204 for personal UV device 202, including inlet 206, outlet 208 and scent tray 212. FIG. 32. Shows a rear view of enclosure 204 for personal UV device 202.

FIG. 33. Shows an exploded perspective front view of personal UV device 202 for use with particulate mask 200 of FIGS. 24-26. UV device 202 includes an impeller 220, control circuit 222, scent tray 212, and power button 234.

FIG. 34. Show side views of a portion of enclosure 204.

FIG. 35. Show side views of the enclosure 204 including a charger port 216.

FIG. 36. Show a side exploded view of enclosure 204 for a personal UV device 202, including batteries 230 and near-field charger 228.

With reference now to FIGS. 37-41, another embodiment of a portable personal air treatment device 302 is shown. Portable personal air treatment device 302 includes a housing 304 defining one or more inlets 306 and one or more outlets 308 and defines an UV irradiation chamber 326 therebetween. Of course, the number and relative position of the inlets and outlets can be arranged in alternate configurations. UV device 302 also includes a reflective material 322 within the UV irradiation chamber and an air impeller 320, e.g., motorized fan or electrohydrodynamic air mover.

Accordingly, the present invention provides a convenient, portable, personal air treatment device. Similarly, while the present invention has been described herein as a portable, personal air treatment device, the present invention may be readily used in any installed, fixed, or public use applications.

Finally, while the present invention has been described above with reference to various exemplary embodiments, many changes, combinations and modifications may be made to the exemplary embodiments without departing from the scope of the present invention. For example, the various components may be implemented in alternative ways. These alternatives can be suitably selected depending upon the particular application or in consideration of any number of factors associated with the operation of the device. In addition, the techniques described herein may be extended or modified for use with other types of devices. These and other changes or modifications are intended to be included within the scope of the present invention.

I claim:

1. A portable personal air treatment device comprising:
an enclosure defining an air pathway;
an impeller for moving air along the air pathway;
a UV source disposed along the air pathway to irradiate pathogens entrained in air within the pathway;
a scent cartridge disposed along the air pathway and configured to disperse a scent into air moving within the pathway;
wherein the scent cartridge is configured to be highly absorbent of oils and to release the oil by evaporation into the air pathway; and
wherein the scent cartridge is exposed to the airflow in the air pathway and is substantially hermetically sealed across scent cartridge surfaces not exposed to the airflow.

2. The personal air treatment device of claim 1, integrated within a personal particulate mask and configured to treat air within the particulate mask.

3. The personal air treatment device of claim 1, further comprising a near-field charger.

4. The personal air treatment device of claim 1, further comprising a processor programmed for logging usage data.

5. The personal air treatment device of claim 4, where the usage data comprises one or more of duration of use, time of use, frequency of use, air quality, and geolocation.

6. The personal air treatment device of claim 1, further comprising a wireless transponder for communicating one or more of a performance parameter, software update, and usage data.

7. The personal air treatment device of claim 6, wherein the personal air treatment device is configured to be controllable via the wireless transponder.

8. The personal air treatment device of claim 6, wherein the personal air treatment device is configured to control an operational status of a plurality of networked personal air treatment devices.

9. A system for scenting air within a region comprising:
a plurality of portable air treatment devices controllable via a wireless protocol to disperse a scent into the air around the air treatment devices;
a controller having a processor programmed to control the plurality of portable air treatment devices via the wireless protocol;
wherein the processor is programmed to selectively coordinate performance parameters of the plurality of portable air treatment devices based on at least one of local weather data, wind conditions, air quality conditions, and geolocation data; and
wherein at least one of the plurality of portable air treatment devices includes a scent cartridge configured to be highly absorbent of oils and to release the oil by evaporation; and wherein the scent cartridge is exposed to the airflow in device and is substantially hermetically sealed across scent cartridge surfaces not exposed to the airflow.

10. The system of claim 9, wherein the processor is programmed to selectively alter at least one of the power state, impeller rate, temperature, and UV irradiation level of a subset of the plurality of portable air treatment devices.

11. The system of claim 9, wherein the processor is programmed to receive user input regarding performance parameter settings for one or more of the plurality of portable air treatment devices.

12. The system of claim 9, wherein the processor is programmed to automatically adjust the performance parameter of one or more of the plurality of the portable air treatment devices.

13. The system of claim 12, wherein the processor is programmed to coordinate performance parameters of the plurality of portable air treatment devices based on the location of a central user device.

14. The system of claim 9, wherein the processor is programmed to coordinate preprogrammed performance parameters of the plurality of air treatment devices including at least one of timed, pulsed, random, alternating, escalating, and calendared device operation.

15. A personal air treatment mask comprising:
a particulate mask; and
an air treatment device disposed within the particulate mask and comprising:
an enclosure defining an air inlet, an air outlet, and an air pathway therebetween;
an impeller for conducting air along the air pathway; and
a UV lamp disposed along the air pathway to treat air circulated within the particulate mask;
a scent cartridge configured to be highly absorbent of oils and to release the oil by evaporation into the air pathway; and
wherein the scent cartridge is exposed to the airflow in the air pathway and is substantially hermetically sealed across scent cartridge surfaces not exposed to the airflow.

16. The personal air treatment mask of claim 15, wherein the air treatment device further comprises a replaceable scent cartridge disposed along the air pathway.

17. The personal air treatment mask of claim 16, further comprising a wireless transponder configured to communicate usage data for the air treatment device via a wireless protocol.

* * * * *